US011085930B2

(12) United States Patent
Nam et al.

(10) Patent No.: US 11,085,930 B2
(45) Date of Patent: *Aug. 10, 2021

(54) ANTI-NRP1 ANTIBODY SCREENING METHOD

(71) Applicant: SAMSUNG LIFE PUBLIC WELFARE FOUNDATION, Seoul (KR)

(72) Inventors: Do-Hyun Nam, Seoul (KR); Jae Hyun Lee, Gyeonggi-do (KR)

(73) Assignee: AIMED BIO INC., Seoul (KR)

(*) Notice: Subject to any disclaimer, the term of this patent is extended or adjusted under 35 U.S.C. 154(b) by 266 days.

This patent is subject to a terminal disclaimer.

(21) Appl. No.: 16/306,568

(22) PCT Filed: Jun. 2, 2017

(86) PCT No.: PCT/KR2017/005767
§ 371 (c)(1),
(2) Date: Dec. 1, 2018

(87) PCT Pub. No.: WO2017/209554
PCT Pub. Date: Dec. 7, 2017

(65) Prior Publication Data
US 2020/0011878 A1    Jan. 9, 2020

(30) Foreign Application Priority Data
Jun. 3, 2016 (KR) .................. 10-2016-0069360
Jun. 2, 2017 (KR) .................. 10-2017-0069141

(51) Int. Cl.
A61P 35/00   (2006.01)
G01N 33/68   (2006.01)
A01K 67/027  (2006.01)
C07K 16/28   (2006.01)
G01N 33/50   (2006.01)
A61K 39/00   (2006.01)

(52) U.S. Cl.
CPC ..... G01N 33/6854 (2013.01); A01K 67/0271 (2013.01); A61P 35/00 (2018.01); C07K 16/2863 (2013.01); G01N 33/5011 (2013.01); A01K 2207/12 (2013.01); A01K 2227/105 (2013.01); A01K 2267/0331 (2013.01); A01K 2267/0387 (2013.01); A61K 2039/505 (2013.01); C07K 2317/565 (2013.01); C07K 2317/567 (2013.01); C07K 2317/622 (2013.01); C07K 2317/73 (2013.01); C07K 2317/76 (2013.01); C07K 2317/77 (2013.01); C07K 2317/92 (2013.01); G01N 2500/10 (2013.01)

(58) Field of Classification Search
CPC .................................................. G01N 33/5011
USPC ........................................................ 800/3
See application file for complete search history.

(56) References Cited

U.S. PATENT DOCUMENTS

| 4,554,101 A | 11/1985 | Hopp |
| 2002/0199212 A1 | 12/2002 | Sone et al. |

FOREIGN PATENT DOCUMENTS

| JP | 2004526940 A1 | 9/2004 |
| JP | 2006516594 A1 | 7/2006 |
| JP | 2009514972 A1 | 4/2009 |
| KR | 1020080068105 A | 7/2008 |
| KR | 10-2012-0048563 A | 5/2012 |
| KR | 1020150105615 A | 9/2015 |
| WO | 8801649 A1 | 3/1988 |
| WO | 8806630 A1 | 9/1988 |
| WO | 8807085 A1 | 9/1988 |
| WO | 8807086 A1 | 9/1988 |
| WO | 8809344 A1 | 12/1988 |
| WO | WO2004097008 A1 | 11/2004 |
| WO | WO2007056470 A2 | 5/2007 |
| WO | 2011143408 A1 | 11/2011 |
| WO | WO2014150314 A1 | 9/2014 |
| WO | WO2016089126 A1 | 6/2016 |

OTHER PUBLICATIONS

Hu et al (Oncogene, 2007, 26: 5577-5586).*
Hoogenboom (Nature Biotechnology, 2005, 23(9): 1105-1116).*
Chang et al (Experimental Cell Research, 2013, 319: 1146-1155).*
Hoogenboom, H.R., "Selecting and Screening Recombinant Antibody Libraries", "Nature Biotechnology", Sep. 2005, pp. 1105-1116, vol. 23, No. 9.
Sandercock, A., et al., "Identification of Anti-Tumour Biologics Using Primary Tumour Models, 3-D Phenotypic Screening and Image-Based Multi-Parametric Profiling", "Molecular Cancer", 2015, pp. 1-18, vol. 14, No. 147.
Zhu, X., et al., "Identification of Internalizing Human Single-Chain Antibodies Targeting Brain Tumor Sphere Cells", "Molecular Cancer Therapeutics", 2010, pp. 2131-2141, vol. 9, No. 7.
Liu, B, et al., "Mapping Tumor Epitope Space by Direct Selection of Single-Chain Fv Antibody Libraries on Prostate Cancer Cells", "Cancer Research", Jan. 15, 2004, pp. 704-710, vol. 64, Publisher: American Association for Cancer.
"Jan. 6, 2012 Notice of Allowance in U.S. Appl. No. 12/831,241, issued by Brian M. Gulledge".
Andersen, P., et al., "A recombinant antibody with the antigen-specific, major histocompatibility complex-restricted specificity of T cells", "Proc. Natl. Acad. Sci.", Mar. 1996, pp. 1820-1824, vol. 93.

(Continued)

Primary Examiner — Sean E Aeder
(74) Attorney, Agent, or Firm — Hultquist, PLLC; Steven J. Hultquist

(57) ABSTRACT

The present disclosure relates to a method of screening an anti-NRP1 antibody or an antigen-binding fragment thereof by use of patient-derived tumor spheroids overexpressing NRP1 and an animal model comprising the same, and more particularly to a method of screening an antibody or an antigen-binding fragment thereof through in vitro and in vivo panning by use of a patient-derived tumor spheroid containing NRP1 and an animal model transplanted with the same, respectively.

6 Claims, 15 Drawing Sheets
(15 of 15 Drawing Sheet(s) Filed in Color)
Specification includes a Sequence Listing.

(56) References Cited

OTHER PUBLICATIONS

Barry, M., et al., "Toward cell-targeting gene therapy vectors: Selection of cell-binding peptides from random peptide-presenting phage libraries", "Nature Medicine", Mar. 1996, pp. 299-305, vol. 2, No. 3, Publisher: Nature Publishing Group.

"https://blast.ncbi.nlm.nih.gov/Blast.cgi?CMD=Web&PAGE_TYPE=BlastNews#1", Dec. 1, 2018.

"www..ncbi.nlm.nih.gov/BLAST", Dec. 1, 2018.

Cai, X., et al., "Anti-melanoma antibodies from melanoma patients immunized with genetically modified autologous tumor cells: Selection of specific antibodies from single-chain Fv fusion phage libraries", "Proc. Natl. Acad.Sci. USA", Jul. 1995, pp. 6537-6541, vol. 92.

Sanchez-Martin, D., et al., "Selection strategies for anti-cancer antibody discovery: searching off the beaten path", "Trends Biotechnol.", 2015, pp. 292-301, vol. 33, No. 5, Publisher: HHS Public Access.

Williams, R., et al., "In Vitro Selection of Cancer Cell-Specific Molecular Recognition Elements from Amino Acid Libraries", "Journal of Immunology Research", 2015, pp. 1-12, vol. 2015, Publisher: Hindawi Publishing Corporation; http://dx.doi.org/10.1155/2015/186586.

Williams, R., et al., "Identification of an antibody fragment specific for androgen-dependent prostate cancer cells", "BMC Biotechnology", 2014, pp. 1-11, vol. 14, No. 81, Publisher: http://www.biomedcentral.com/1472-6750/14/81.

Yang, H., et al., "Construction of a Large Synthetic Human scFv Library with Six Diversified CDRs and High Functional Diversity", "Mol. Cells", Feb. 28, 2009, pp. 225-235, vol. 27, Publisher: Springer.

Gustafson, H.H., et al., "Current state of in vivo panning technologies: Designing specificity and affinity into the future of drug targeting", Advanced Druge Delivery Reviews, 2018, p. doi:10.1016/j.addr.2018.06.015.

Laakkonen, P., et al., "A tumor-homing peptide with a targeting specificity related to lymphatic vessels", Nature Medicine, 2002, pp. 751-755, vol. 8, No. 7, Jul. 2002, Publisher: Nature Publishing Group.

Pan, Q., et al., "Blocking Neuropilin-1 Function Has an Additive Effect with Anti-VEGF to Inhibit Tumor Growth", Cancer Cell, Jan. 2007, pp. 53-67, vol. 11, Publisher: Elsevier, Inc.

* cited by examiner

[Fig. 1]
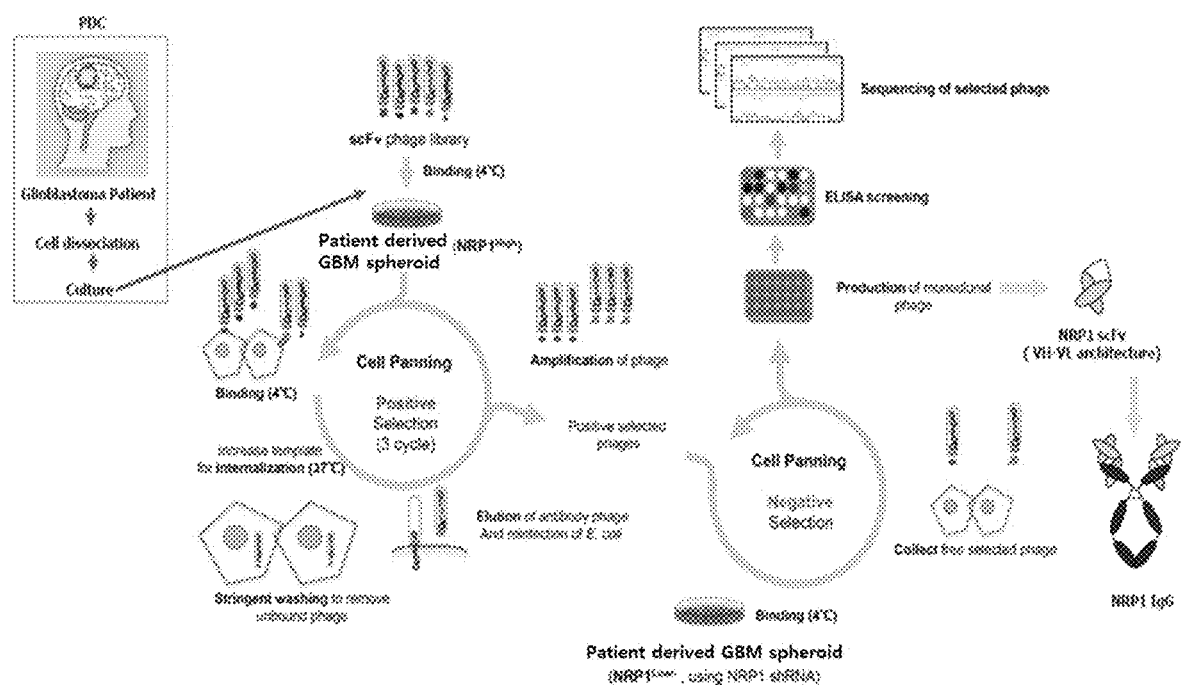

[Fig. 2]
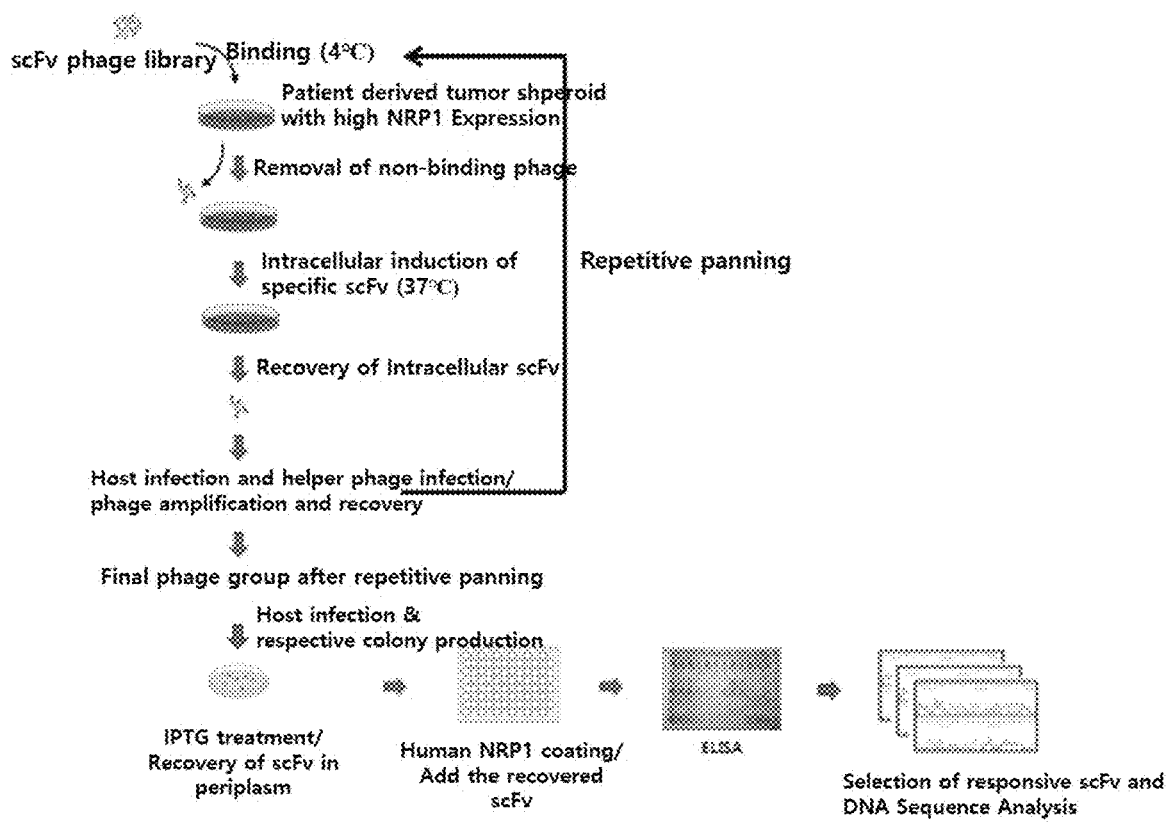
[Fig. 3]
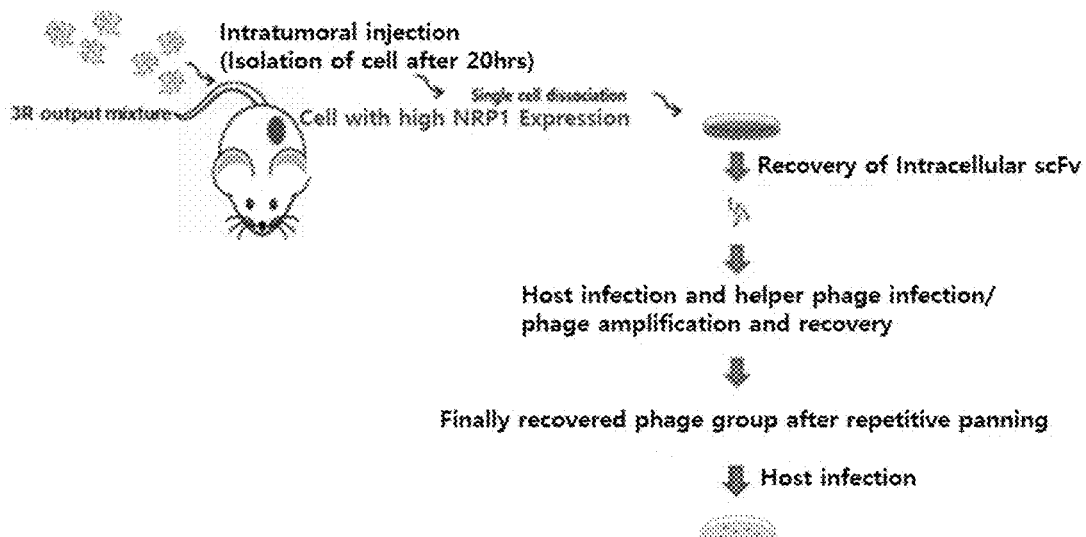

[Fig. 4]
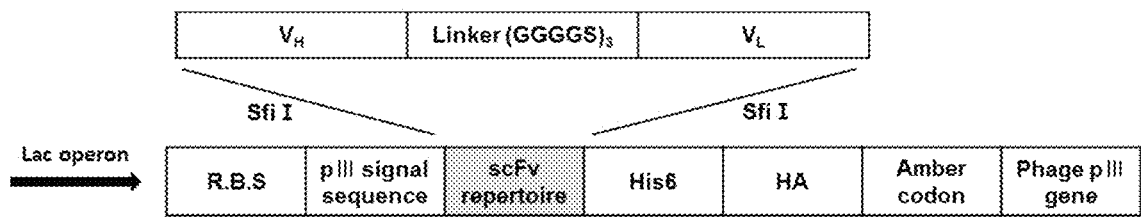
[Fig. 5]
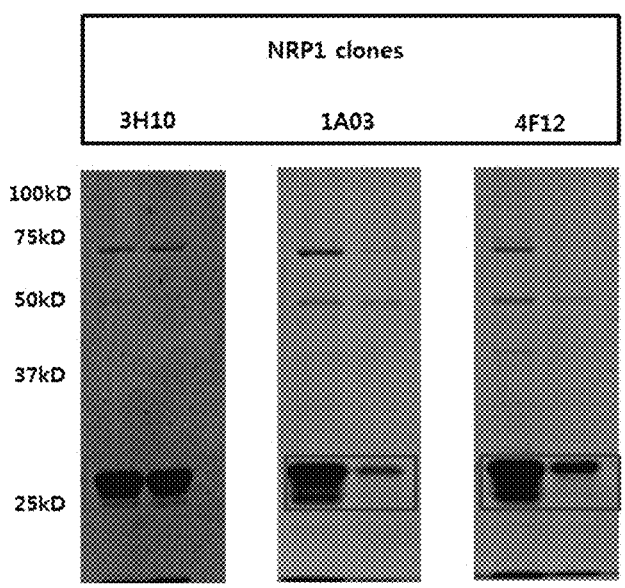
[Fig. 6]
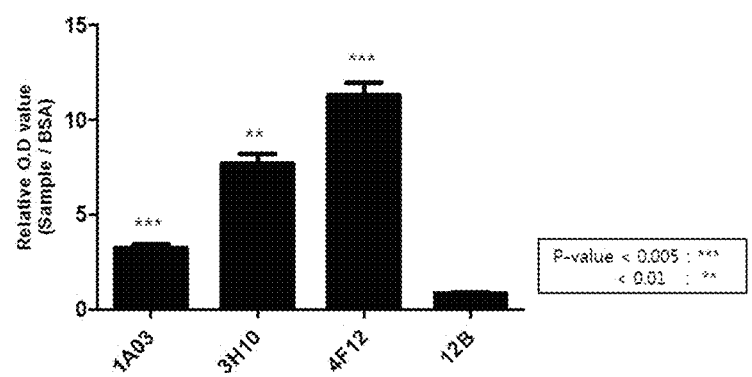

[Fig. 7]
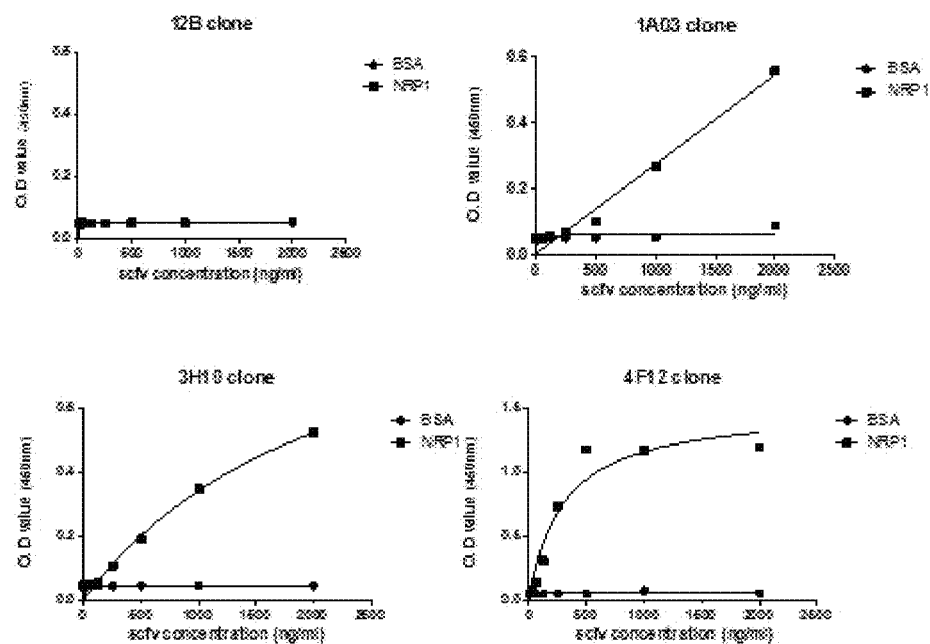
[Fig. 8]
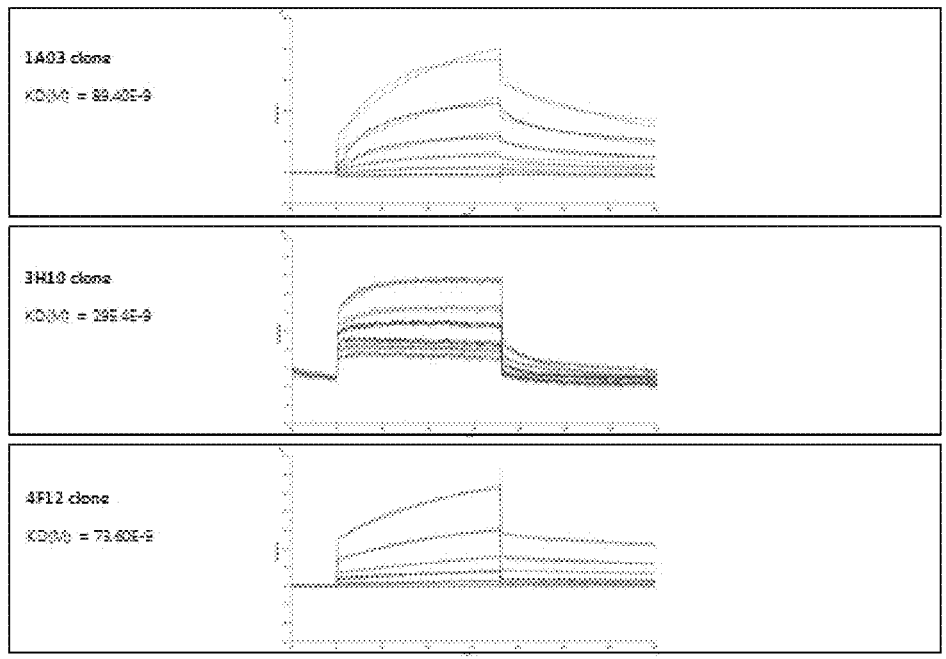

[Fig. 9]
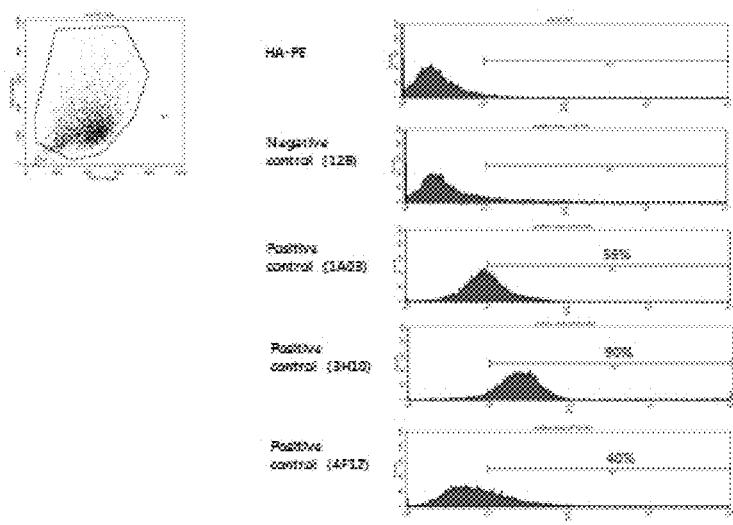
[Fig. 10a]
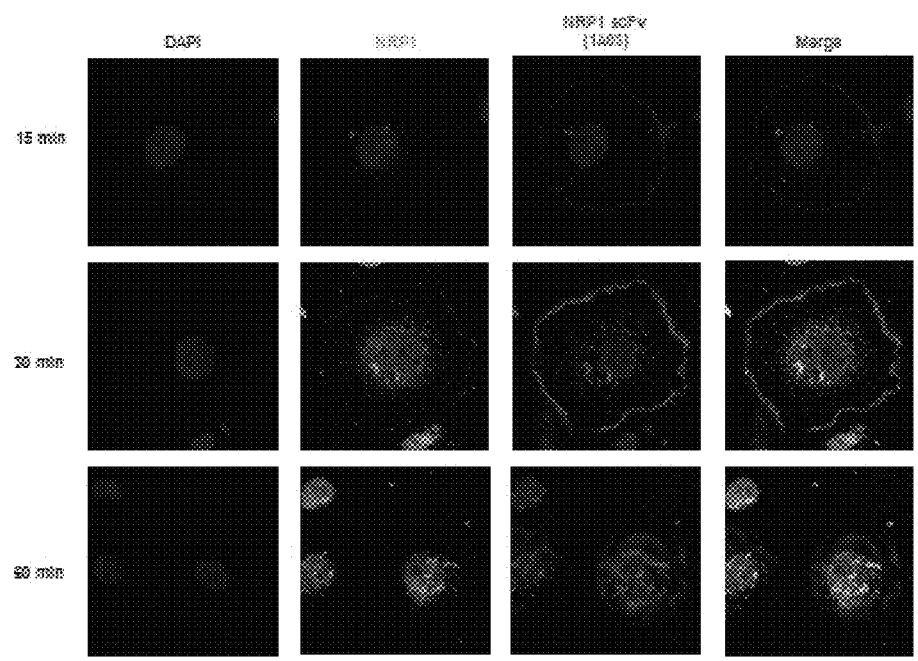

[Fig. 10b]
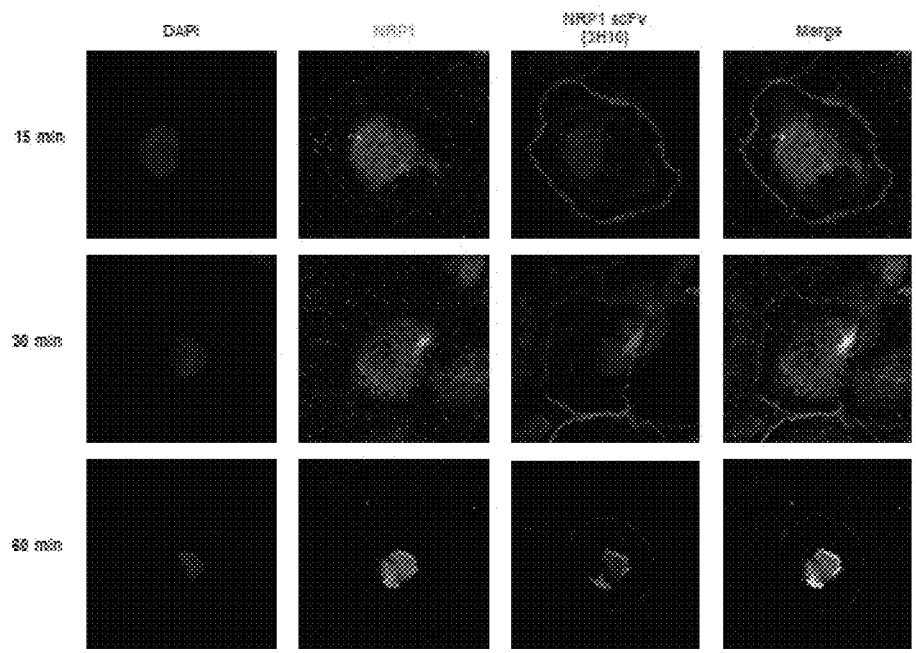
[Fig. 10c]
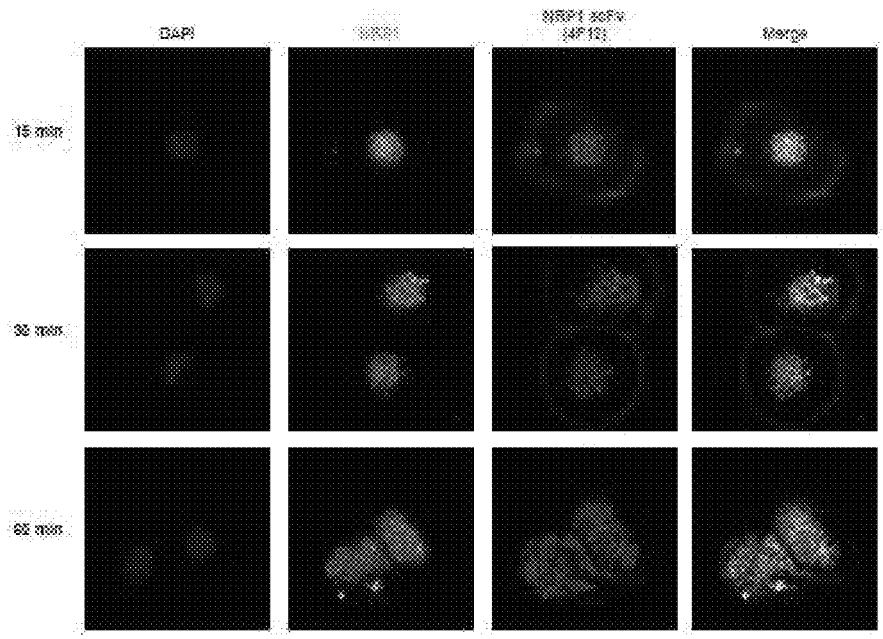

[Fig. 11]
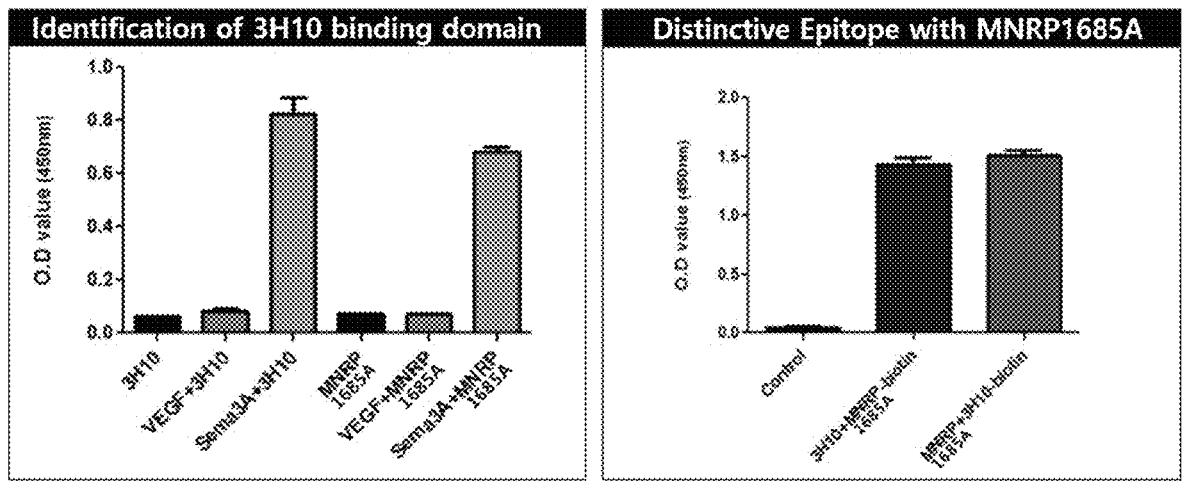
[Fig. 12]
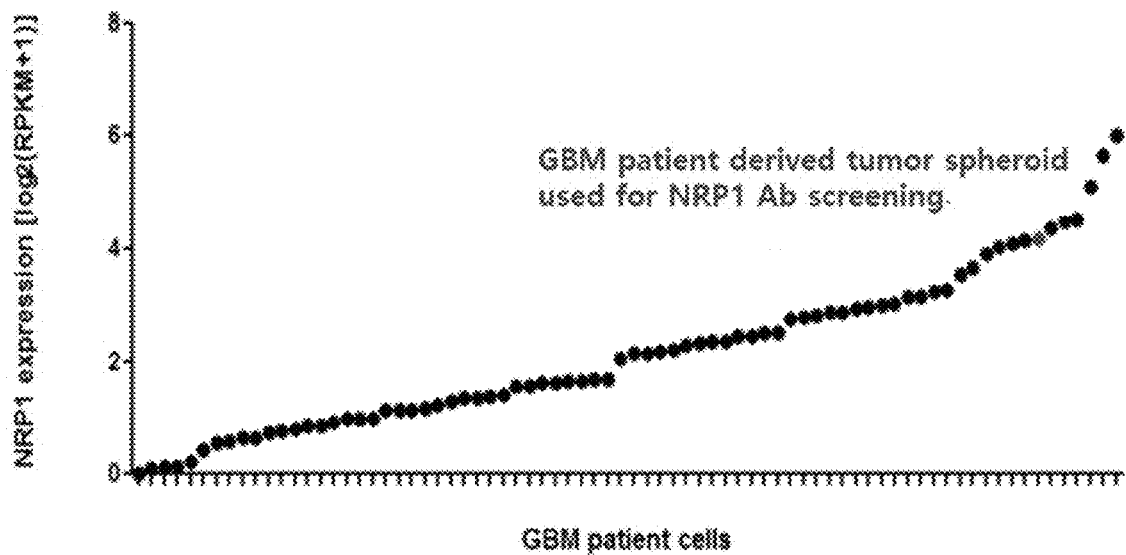

[Fig. 13]
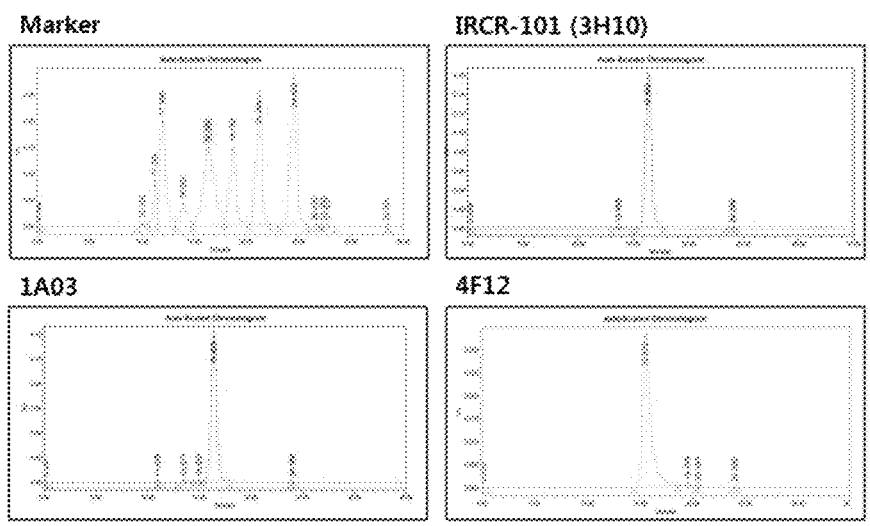
[Fig. 14]
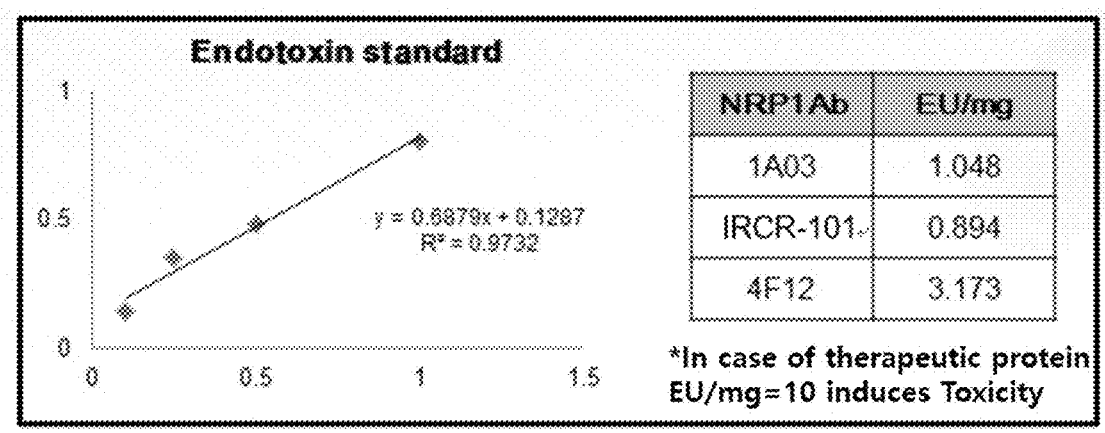

[Fig. 15]
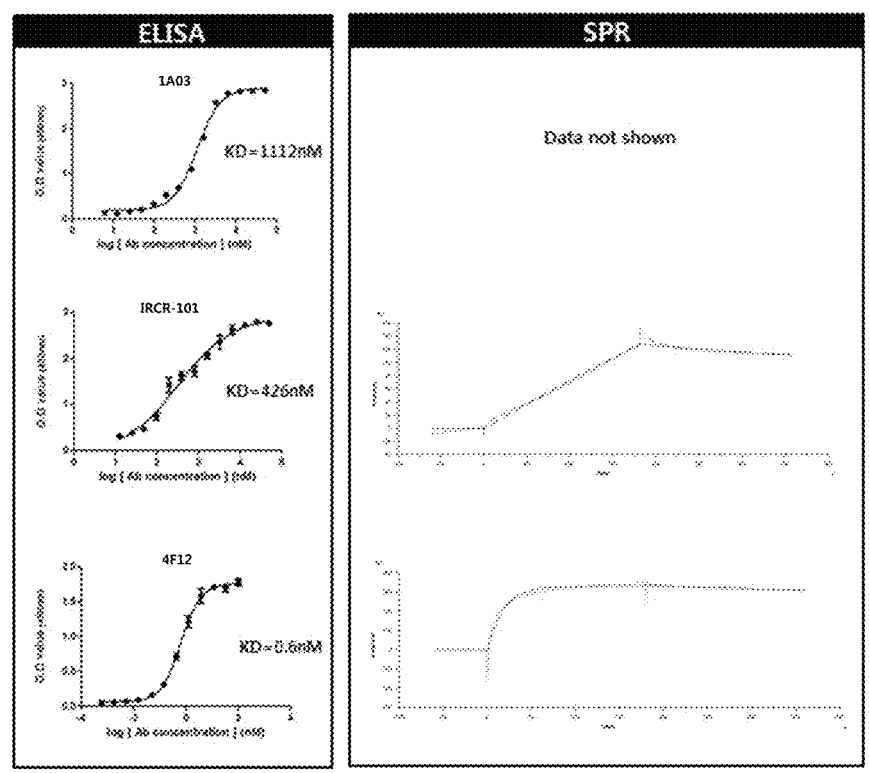

[Fig. 16]
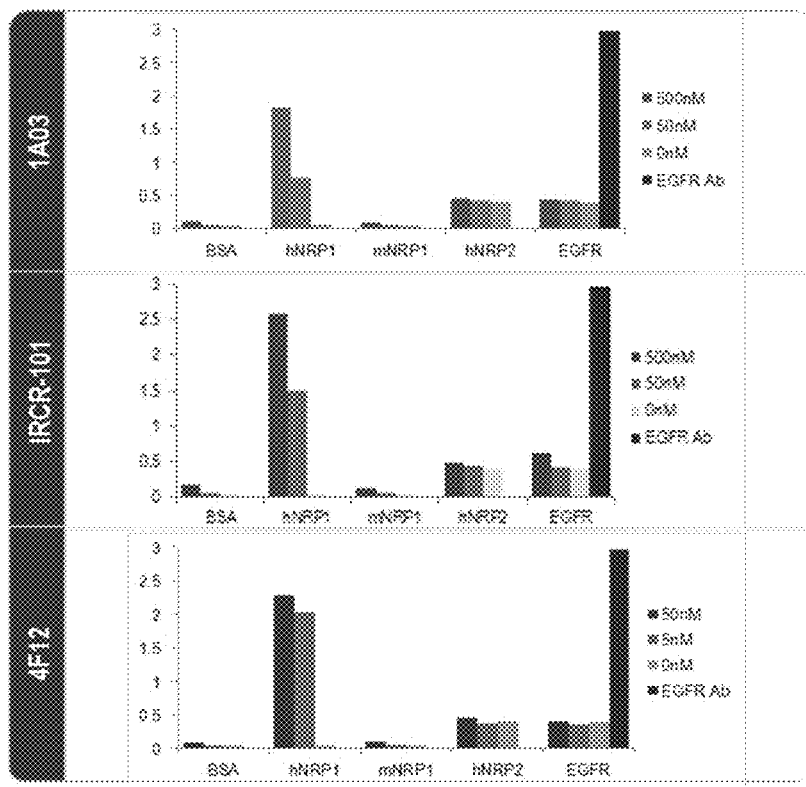
[Fig. 17]
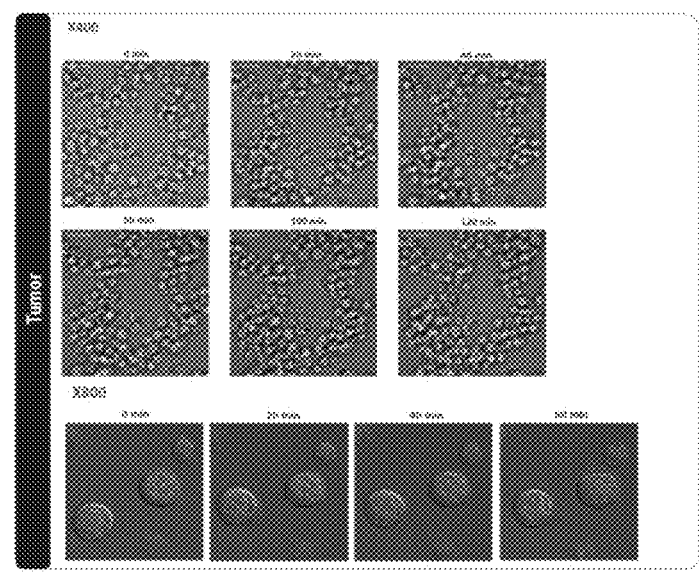

[Fig. 18]
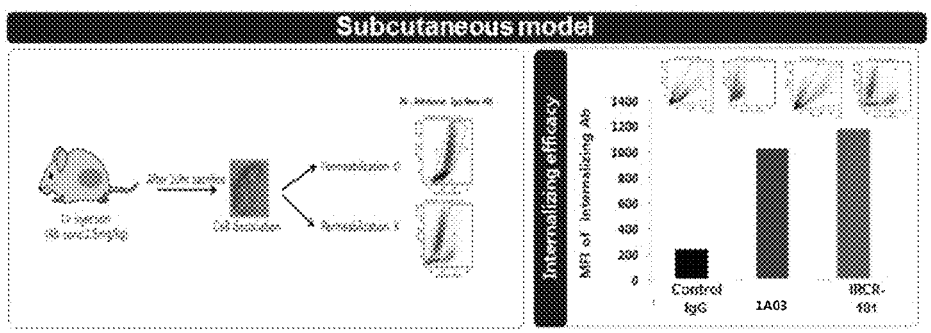
[Fig. 19]
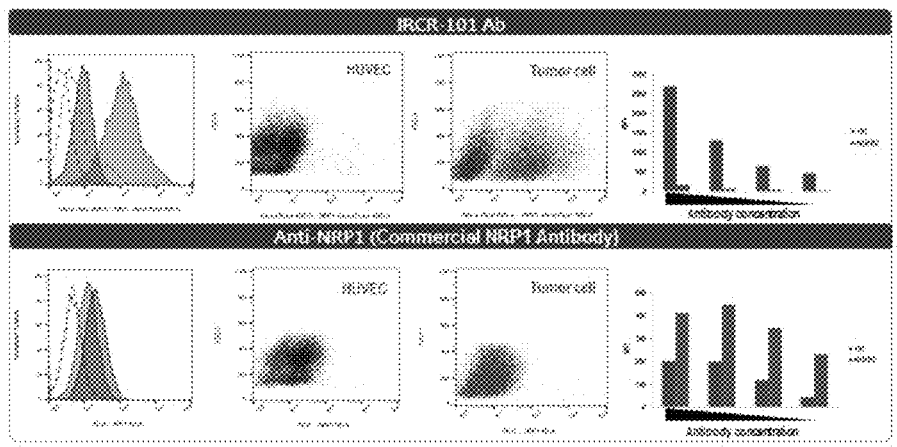
[Fig. 20]
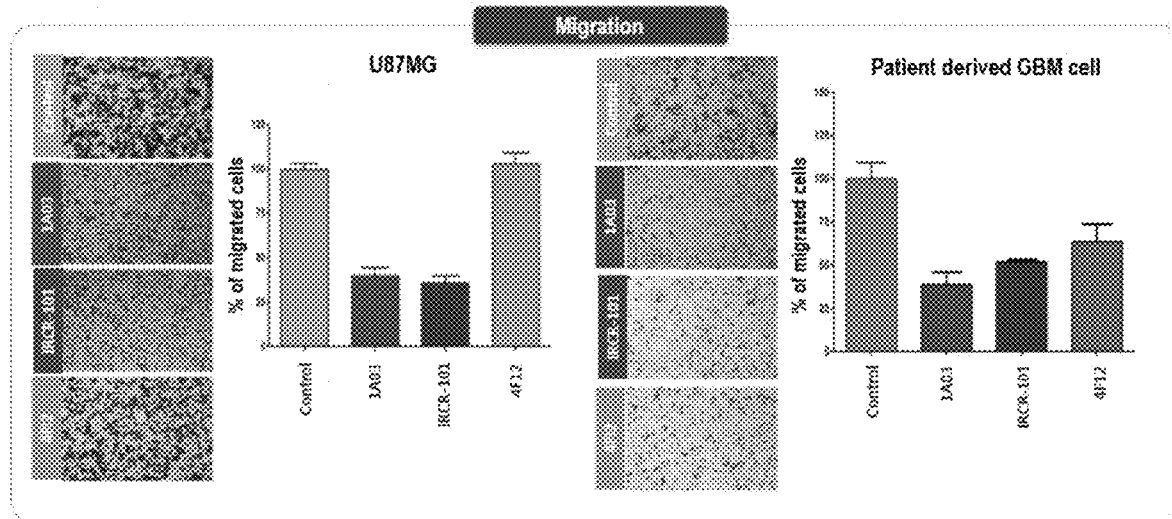

[Fig. 21]
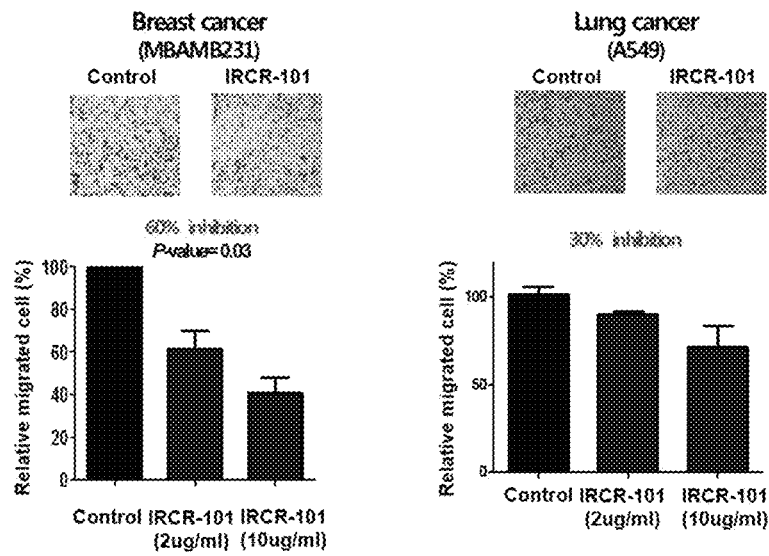
[Fig. 22]
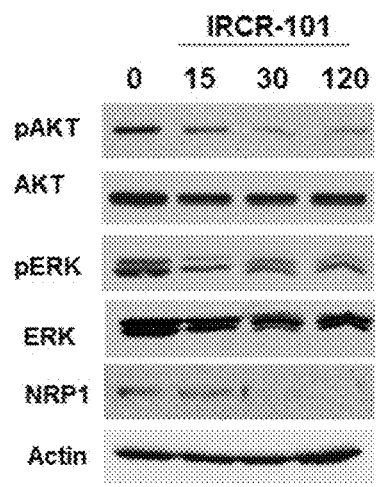

[Fig. 23]
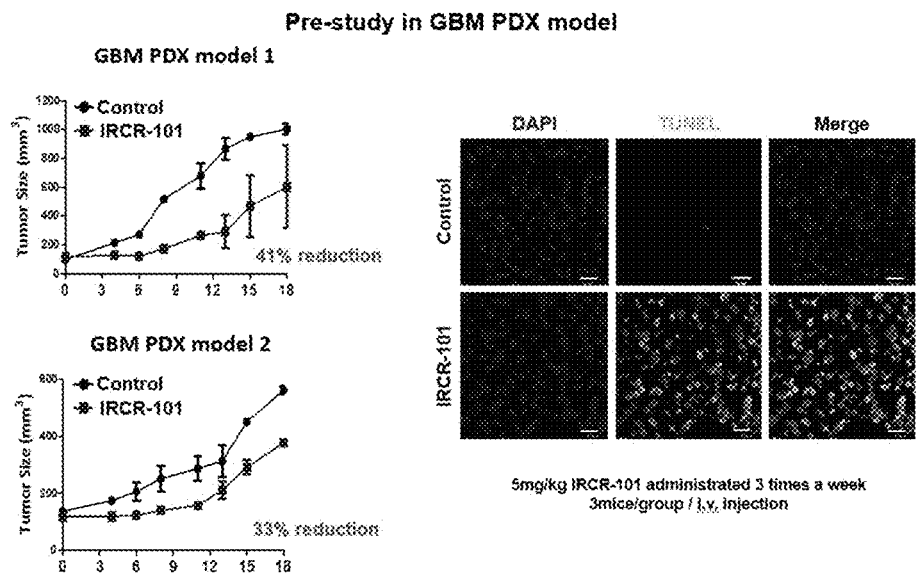
[Fig. 24]
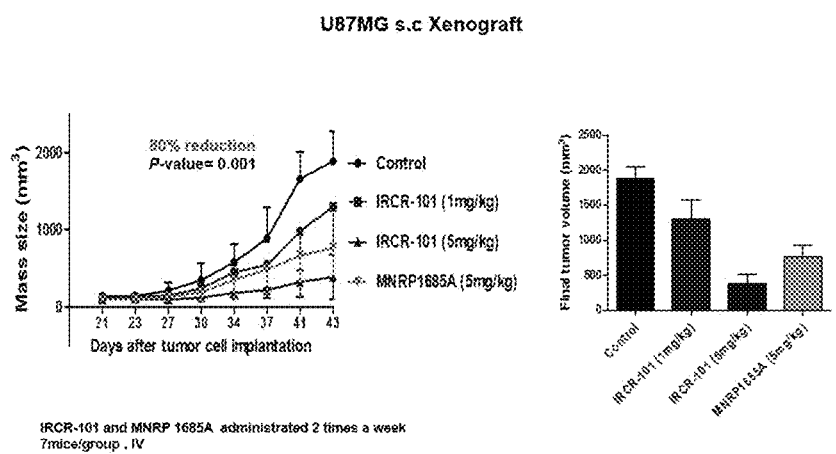

[Fig. 25]
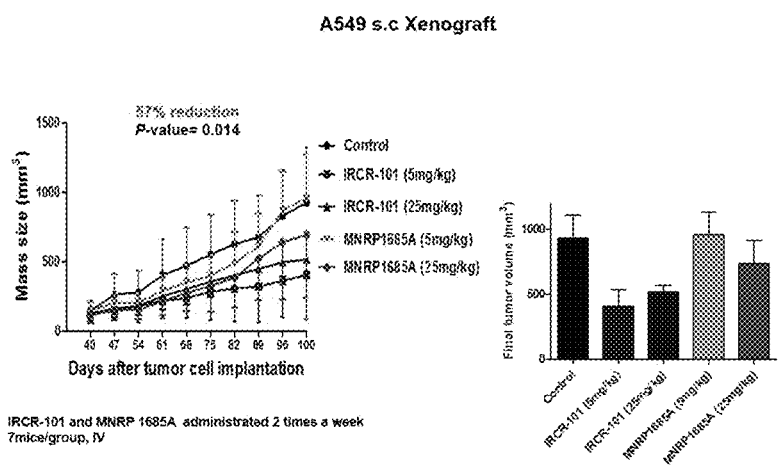
[Fig. 26]
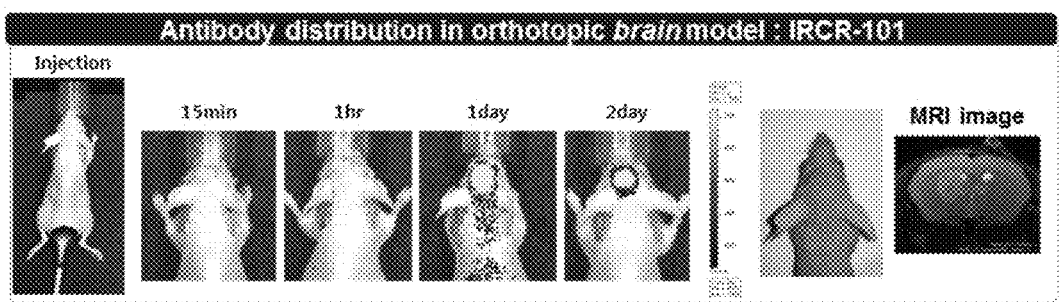

[Fig. 27]
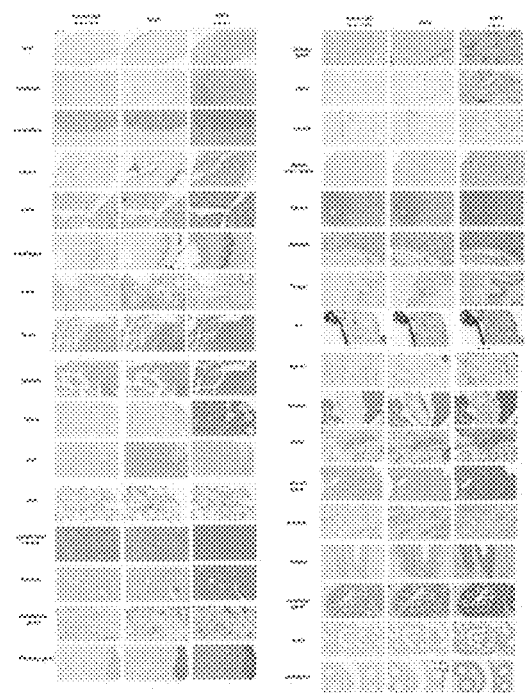

SEQUENCE LISTING

```
<160> NUMBER OF SEQ ID NOS: 40

<210> SEQ ID NO 1
<211> LENGTH: 15
<212> TYPE: PRT
<213> ORGANISM: Artificial Sequence
<220> FEATURE:
<223> OTHER INFORMATION: Phagemid vector linker

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 25
<212> TYPE: PRT
<213> ORGANISM: Artificial Sequence
<220> FEATURE:
<223> OTHER INFORMATION: 1A03 heavy chain FR1

<400> SEQUENCE: 2

Glu Val Gln Leu Leu Glu Ser Gly Gly Gly Leu Val Gln Phe Gly Gly
1               5                   10                  15

Ser Leu Arg Leu Ser Gln Ala Ala Ser
            20                  25

<210> SEQ ID NO 3
<211> LENGTH: 8
<212> TYPE: PRT
<213> ORGANISM: Artificial Sequence
<220> FEATURE:
<223> OTHER INFORMATION: 1A03 heavy chain CDR1

<400> SEQUENCE: 3

Gly Phe Thr Phe Ser Ser Tyr Tyr
1               5
```

```
<210> SEQ ID NO 4
<211> LENGTH: 17
<212> TYPE: PRT
<213> ORGANISM: Artificial Sequence
<220> FEATURE:
<223> OTHER INFORMATION: 1A03 heavy chain FR2

<400> SEQUENCE: 4

Met Ser Trp Val Arg Gln Ala Phe Gly Lys Gly Leu Glu Trp Val Ser
1               5                   10                  15

Ala

<210> SEQ ID NO 5
<211> LENGTH: 8
<212> TYPE: PRT
<213> ORGANISM: Artificial Sequence
<220> FEATURE:
<223> OTHER INFORMATION: 1A03 heavy chain CDR2

<400> SEQUENCE: 5

Ile Ser Phe Gly Ser Ser Asn Lys
1               5

<210> SEQ ID NO 6
<211> LENGTH: 38
<212> TYPE: PRT
<213> ORGANISM: Artificial Sequence
<220> FEATURE:
<223> OTHER INFORMATION: 1A03 heavy chain FR3

<400> SEQUENCE: 6

Tyr Tyr Ala Asp Ser Val Gln Gly Arg Phe Thr Ile Ser Arg Asp Asn
1               5                   10                  15

Ser Lys Asn Thr Leu Tyr Leu Gln Met Asn Glu Leu Arg Ala Glu Asp
            20                  25                  30

Thr Ala Val Tyr Tyr Cys
            35

<210> SEQ ID NO 7
<211> LENGTH: 9
<212> TYPE: PRT
<213> ORGANISM: Artificial Sequence
<220> FEATURE:
<223> OTHER INFORMATION: 1A03 heavy chain CDR3

<400> SEQUENCE: 7

Ala Arg Arg Lys Lys Ser Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: 1A03 heavy chain FR4

<400> SEQUENCE: 8

Trp Gly Gln Gly Thr Leu Val Thr Val Ser Ser
1               5                   10

<210> SEQ ID NO 9
<211> LENGTH: 25
<212> TYPE: PRT
<213> ORGANISM: Artificial Sequence
```

<220> FEATURE:
<223> OTHER INFORMATION: 3H10 heavy chain FR1

<400> SEQUENCE: 9

Glu Val Gln Leu Leu Glu Ser Gly Gly Gly Leu Val Gln Phe Gln Gln
1               5                   10                  15

Ser Leu Arg Leu Ser Gln Ala Ala Ser
            20                  25

<210> SEQ ID NO 10
<211> LENGTH: 8
<212> TYPE: PRT
<213> ORGANISM: Artificial Sequence
<220> FEATURE:
<223> OTHER INFORMATION: 3H10 heavy chain CDR1

<400> SEQUENCE: 10

Gln Phe Thr Phe Ser Ser Tyr Tyr
1               5

<210> SEQ ID NO 11
<211> LENGTH: 17
<212> TYPE: PRT
<213> ORGANISM: Artificial Sequence
<220> FEATURE:
<223> OTHER INFORMATION: 3H10 heavy chain FR2

<400> SEQUENCE: 11

Met Ser Trp Val Arg Gln Ala Phe Gly Lys Gly Leu Glu Trp Val Ser
1               5                   10                  15

Ala

<210> SEQ ID NO 12
<211> LENGTH: 8
<212> TYPE: PRT
<213> ORGANISM: Artificial Sequence
<220> FEATURE:
<223> OTHER INFORMATION: 3H10 heavy chain CDR2

<400> SEQUENCE: 12

Ile Ser Pro Gly Ser Ser Asn Lys
1               5

<210> SEQ ID NO 13
<211> LENGTH: 38
<212> TYPE: PRT
<213> ORGANISM: Artificial Sequence
<220> FEATURE:
<223> OTHER INFORMATION: 3H10 heavy chain FR3

<400> SEQUENCE: 13

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Glu Leu Arg Ala Glu Asp
            20                  25                  30

Thr Ala Val Tyr Tyr Cys
        35

<210> SEQ ID NO 14
<211> LENGTH: 9
<212> TYPE: PRT
<213> ORGANISM: Artificial Sequence
<220> FEATURE:
<223> OTHER INFORMATION: 3H10 heavy chain CDR3

```
<400> SEQUENCE: 14

Ala Arg Arg Lys Tyr Met Phe Asp Tyr
1               5

<210> SEQ ID NO 15
<211> LENGTH: 11
<212> TYPE: PRT
<213> ORGANISM: Artificial Sequence
<220> FEATURE:
<223> OTHER INFORMATION: 3H10 heavy chain FR4

<400> SEQUENCE: 15

Trp Gly Gln Gly Thr Leu Val Thr Val Ser Ser
1               5                   10

<210> SEQ ID NO 16
<211> LENGTH: 25
<212> TYPE: PRT
<213> ORGANISM: Artificial Sequence
<220> FEATURE:
<223> OTHER INFORMATION: 4F12 heavy chain FR1

<400> SEQUENCE: 16

Glu Val Gln Leu Leu Glu Ser Gly Gly Gly Leu Val Gln Phe Gly Gly
1               5                   10                  15

Ser Leu Arg Leu Ser Gln Ala Ala Ser
            20                  25

<210> SEQ ID NO 17
<211> LENGTH: 8
<212> TYPE: PRT
<213> ORGANISM: Artificial Sequence
<220> FEATURE:
<223> OTHER INFORMATION: 4F12 heavy chain CDR1

<400> SEQUENCE: 17

Gly Phe Thr Phe Ser Gly Tyr Ala
1               5

<210> SEQ ID NO 18
<211> LENGTH: 17
<212> TYPE: PRT
<213> ORGANISM: Artificial Sequence
<220> FEATURE:
<223> OTHER INFORMATION: 4F12 heavy chain FR2

<400> SEQUENCE: 18

Met Ser Trp Val Arg Gln Ala Phe Gly Lys Gly Leu Glu Trp Val Ser
1               5                   10                  15

Gly

<210> SEQ ID NO 19
<211> LENGTH: 8
<212> TYPE: PRT
<213> ORGANISM: Artificial Sequence
<220> FEATURE:
<223> OTHER INFORMATION: 4F12 heavy chain CDR2

<400> SEQUENCE: 19

Ile Ser Pro Gly Ser Gly Ser Thr
1               5

<210> SEQ ID NO 20
<211> LENGTH: 38
<212> TYPE: PRT
```

```
<213> ORGANISM: Artificial Sequence
<220> FEATURE:
<223> OTHER INFORMATION: 4F12 heavy chain FR3

<400> SEQUENCE: 20

Tyr Tyr Ala Asp Ser Val Lys Gly Arg Phe Thr Ile Ser Arg Asp Asn
1               5                   10                  15

Glu Lys Asn Thr Leu Tyr Leu Gln Met Asn Glu Leu Arg Ala Glu Asp
            20                  25                  30

Thr Ala Val Tyr Tyr Cys
        35

<210> SEQ ID NO 21
<211> LENGTH: 9
<212> TYPE: PRT
<213> ORGANISM: Artificial Sequence
<220> FEATURE:
<223> OTHER INFORMATION: 4F12 heavy chain CDR3

<400> SEQUENCE: 21

Ala Lys Arg Lys Thr Arg Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: 4F12 heavy chain FR4

<400> SEQUENCE: 22

Trp Gly Gln Gly Thr Leu Val Thr Val Ser Ser
1               5                   10

<210> SEQ ID NO 23
<211> LENGTH: 25
<212> TYPE: PRT
<213> ORGANISM: Artificial Sequence
<220> FEATURE:
<223> OTHER INFORMATION: 1A03 light chain FR1

<400> SEQUENCE: 23

Gln Ser Val Leu Thr Gln Phe Phe Ser Ala Ser Gly Thr Pro Gly Gln
1               5                   10                  15

Arg Val Thr Ile Ser Cys Ser Gly Phe
            20                  25

<210> SEQ ID NO 24
<211> LENGTH: 8
<212> TYPE: PRT
<213> ORGANISM: Artificial Sequence
<220> FEATURE:
<223> OTHER INFORMATION: 1A03 light chain CDR1

<400> SEQUENCE: 24

Ser Ser Asn Ile Gly Asn Asn Asp
1               5

<210> SEQ ID NO 25
<211> LENGTH: 17
<212> TYPE: PRT
<213> ORGANISM: Artificial Sequence
<220> FEATURE:
<223> OTHER INFORMATION: 1A03 light chain FR2

<400> SEQUENCE: 25
```

Val Ser Trp Tyr Gln Gln Leu Phe Gly Thr Ala Pro Lys Leu Leu Ile
1               5                   10                  15

Tyr

<210> SEQ ID NO 26
<211> LENGTH: 36
<212> TYPE: PRT
<213> ORGANISM: Artificial Sequence
<220> FEATURE:
<223> OTHER INFORMATION: 1A03 light chain FR3

<400> SEQUENCE: 26

Asn Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Asp Glu Ala
            20                  25                  30

Asp Tyr Tyr Cys
        35

<210> SEQ ID NO 27
<211> LENGTH: 11
<212> TYPE: PRT
<213> ORGANISM: Artificial Sequence
<220> FEATURE:
<223> OTHER INFORMATION: 1A03 light chain CDR3

<400> SEQUENCE: 27

Gly Ala Trp Val Ala Ser Leu Ser Ala Tyr Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: 1A03 light chain FR4

<400> SEQUENCE: 28

Phe Gly Gly Gly Thr Lys Leu Thr Val Thr Leu
1               5                   10

<210> SEQ ID NO 29
<211> LENGTH: 25
<212> TYPE: PRT
<213> ORGANISM: Artificial Sequence
<220> FEATURE:
<223> OTHER INFORMATION: 3H10 light chain FR1

<400> SEQUENCE: 29

Gly Ser Val Leu Thr Gln Pro Pro Ser Ala Ser Gly Thr Pro Gly Gln
1               5                   10                  15

Arg Val Thr Ile Ser Cys Thr Gly Glu
            20                  25

<210> SEQ ID NO 30
<211> LENGTH: 8
<212> TYPE: PRT
<213> ORGANISM: Artificial Sequence
<220> FEATURE:
<223> OTHER INFORMATION: 3H10 light chain CDR1

<400> SEQUENCE: 30

Ser Ser Asn Ile Gly Asn Asn Asp
1               5

```
<210> SEQ ID NO 31
<211> LENGTH: 17
<212> TYPE: PRT
<213> ORGANISM: Artificial Sequence
<220> FEATURE:
<223> OTHER INFORMATION: 3H10 light chain FR2

<400> SEQUENCE: 31

Val Tyr Trp Tyr Gln Gln Leu Pro Gly Thr Ala Phe Lys Leu Leu Ile
1               5                   10                  15

Tyr

<210> SEQ ID NO 32
<211> LENGTH: 36
<212> TYPE: PRT
<213> ORGANISM: Artificial Sequence
<220> FEATURE:
<223> OTHER INFORMATION: 3H10 light chain FR3

<400> SEQUENCE: 32

Asn Arg Pro Ser Gly Met Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 33
<211> LENGTH: 11
<212> TYPE: PRT
<213> ORGANISM: Artificial Sequence
<220> FEATURE:
<223> OTHER INFORMATION: 3H10 light chain CDR3

<400> SEQUENCE: 33

Ala Ser Trp Asp Ser Ser Leu Ser Gly Tyr Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: 3H10 light chain FR4

<400> SEQUENCE: 34

Phe Gly Gly Gly Thr Lys Leu Thr Val Thr Leu
1               5                   10

<210> SEQ ID NO 35
<211> LENGTH: 25
<212> TYPE: PRT
<213> ORGANISM: Artificial Sequence
<220> FEATURE:
<223> OTHER INFORMATION: 4F12 light chain FR1

<400> SEQUENCE: 35

Gln Ser Val Leu Thr Gln Phe Phe Ser Ala Ser Gly Thr Phe Gly Arg
1               5                   10                  15

Arg Val Thr Ile Ser Gln Ser Gly Ser
            20                  25

<210> SEQ ID NO 36
```

```
<211> LENGTH: 8
<212> TYPE: PRT
<213> ORGANISM: Artificial Sequence
<220> FEATURE:
<223> OTHER INFORMATION: 4F12 light chain CDR1

<400> SEQUENCE: 36

Ser Ser Asn Ile Gly Asn Asn Glu
1               5

<210> SEQ ID NO 37
<211> LENGTH: 17
<212> TYPE: PRT
<213> ORGANISM: Artificial Sequence
<220> FEATURE:
<223> OTHER INFORMATION: 4F12 light chain FR2

<400> SEQUENCE: 37

Val Tyr Trp Tyr Gln Gln Leu Pro Gly Thr Ala Pro Lys Leu Leu Ile
1               5                   10                  15

Tyr

<210> SEQ ID NO 38
<211> LENGTH: 36
<212> TYPE: PRT
<213> ORGANISM: Artificial Sequence
<220> FEATURE:
<223> OTHER INFORMATION: 4F12 light chain FR3

<400> SEQUENCE: 38

Lys Arg Phe Ser Gly Met Pro Asp Arg Phe Ser Gly Ser Lys Glu Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 39
<211> LENGTH: 11
<212> TYPE: PRT
<213> ORGANISM: Artificial Sequence
<220> FEATURE:
<223> OTHER INFORMATION: 4F12 light chain CDR3

<400> SEQUENCE: 39

Ala Ala Trp Asp Ser Ser Leu Asn Gly Tyr Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: 4F12 light chain FR4

<400> SEQUENCE: 40

Phe Gly Gly Gly Thr Lys Leu Thr Val Thr Leu
1               5                   10
```

ANTI-NRP1 ANTIBODY SCREENING METHOD

CROSS-REFERENCE TO RELATED APPLICATIONS

This application is a U.S. national phase under the provisions of 35 U.S.C. § 371 of International Patent Application No. PCT/KR17/05767 filed Jun. 2, 2017, which in turn claims priority of Korean Patent Application No. 10-2016-0069360 filed Jun. 3, 2016 and Korean Patent Application No. 10-2017-0069141 filed Jun. 2, 2017. The disclosures of such international patent application and priority Korean patent applications are hereby incorporated herein by reference in their respective entireties, for all purposes.

TECHNICAL FIELD

The present disclosure relates to a method of screening an anti-NRP1 antibody or an antigen-binding fragment thereof by use of patient-derived tumor spheroids overexpressing NRP1 and an animal model comprising the same, and more particularly to a method of screening an antibody or an antigen-binding fragment thereof through in vitro and in vivo panning by use of a patient-derived tumor spheroid containing NRP1 and an animal model transplanted with the same, respectively.

BACKGROUND ART

Neuropilin (NRP) includes NRP1 and NRP2, which was first discovered in the nerve cells. It was known that NRP1 is composed of about 923 amino acids and NRP2 is composed of about 926 amino acids. Further, they have a similar domain structure in common and thus have an amino acid homology of 44% in total.

Neuropilin (NRP) includes NRP1 and NRP2, which was first discovered in the nerve cells. It is known that NRP1 is composed of about 923 amino acids and NRP2 is composed of about 926 amino acids. Further, NRP1 and NRP2 have a similar domain structure in common and thus have an amino acid homology of 44% in total.

NRP1 is known as a receptor binding to the semaphorin 3A ligand, which acts on the plexin adjuvant-receptor to adjust axonal induction. It has then been found that NRP1 is bound to members of the vascular endothelial growth factor (VEGF) ligand family and thus mediates angiogenesis.

Numerous physiological processes and pathological processes occur through the development of the vascular system. Blood must be adequately supplied to actively growing tissues such as a tumor. These tissues typically produce pro-angiogenic factors that promote new blood vessel formation and maintenance so as to supply blood through angiogenesis. Angiogenesis is not a simple process, but is accomplished through the following steps that: a) endothelial cells (EC) are proliferated or differentiated from existing endothelial cells; b) endothelial cells migrate and coalesce to form a cord-like structure; c) the blood vessel cord progresses tubule formation and forms a vessel having a lumen in the center; d) buds of existing cords or blood vessels begin to form secondary blood vessels; e) the primitive plexus proceeds with further regrowth and regeneration; and f) endothelial cells are placed in endothelial tubes to provide maintenance and adjustment functions for blood vessels (These cells include pericyte cells in the case of small capillaries, smooth muscle cells in the case of large blood vessels, and cardiac myocytes in the heart).

NRP1 is known to be expressed in a variety of human tumor cell lines and human tumors (such as glioblastoma, astrocytoma, glioma, neuroblastoma, testicular cancer, colorectal cancer, melanoma, pancreatic cancer, lung cancer, breast cancer, esophageal cancer, and prostate cancer). NRP1 is also known to be involved in the effects of proliferation, survival and metastasis of cancer cells of VEGF and semaphorin. Further, it is known that the degree of cancer progression increases or the prognosis of cancer patients is poor according to the degree of NRP1 expression.

When tumors grow, angiogenesis is crucial in the transition from hyperplasia to neoplasia and may play a crucial role in providing nutrients for tumor growth and metastasis. The neovascularization allows the tumor cells to gain growth advantage and proliferative autonomy compared to normal cells. Tumors typically start as single abnormal cells that can proliferate in only few cubic millimeters because of the distance from the available capillary layer and can become stagnant in a "latent" state for extended periods of time without further growth and transmission. Subsequently, some tumor cells are converted into angiogenic phenotypes, activating endothelial cells, and proliferating and maturing into new capillaries. These newly formed blood vessels not only allow the primary tumor to grow continuously, but can also propagate and re-colonize metastatic tumor cells.

In this regard, an anti-NRP1 antibody capable of binding with high affinity to NRP1 and inhibiting the growth of cancer cells is required in order to treat cancers in which NRP1 is overexpressed.

Antibody drugs are growing most rapidly in the field of biopharmaceuticals due to their high therapeutic effects and targeted therapeutic properties. The antibody drug market which is the fastest-growing field among 200 biopharmaceuticals accounts for a high proportion (37%) of the total biopharmaceutical market, and the global market for the antibody drugs is expected to grow at an average annual rate of 11.8% as US $51.5 billion in 2012, reaching US $89.9 billion in 2017 (2013 Biopharmaceutics Trend Report, the Korean Ministry of Trade, Industry and Energy, 2013).

Diseases which are the major targets of antibody drugs are mostly concentrated in specific diseases such as such as intractable cancer (49%) and immune diseases (35%), and thus market competition among products with similar indications is intense. Nevertheless, there are subdivided therapeutic targets within diseases, so the field of development of antibody therapeutic drugs for anticancer therapy is determined to continue to grow in the future.

The technology used to identify and secure antibody candidates which are the major active ingredients of these antibody drugs may largely be classified into the development of chimeric or humanized antibodies using hybridoma cell lines, methods employing transgenic mice, and methods employing antibody display technology.

In 1975, a hybridoma technology was developed which produces monoclonal antibodies using hybrid cells formed by fusing cancer cells with normal cells. Since then, the active development of antibody drugs has started, and technologies have been developed which identify humanized antibodies and human antibodies have been developed in order to solve the HAMA (human-anti-mouse antibody) reaction that occurs when mouse monoclonal antibodies are applied to humans.

The technical field for producing human antibodies can be exemplified by transgenic mice and antibody display technologies (phage display, yeast display, ribosome display, etc.). The development of antibodies using transgenic mice, which has recently been most frequently attempted, is a technology that produces human monoclonal antibodies by applying the existing hybridoma technology to transgenic mice transplanted with human antibody genes. This technology has great advantages in that it can produce a high-affinity antibody due to possible in vivo maturation and can effectively produce a human antibody. However, it has disadvantages in that the use conditions of transgenic mice are expensive and there is difficulty in technical entry, such as production know-how.

Among antibody display technologies, phage display technologies are technologies of screening antibodies by displaying antibody fragments on the surface of bacteriophages, and display technologies based on M13 PIII phage are most widely used. However, these phase display technologies have a difficulty in screening cell surface proteins (such as G-protein receptor) or antibodies difficult to express recombinantly, because antibody fragments expressed by gene recombination are displayed on the surface of bacteriophages.

In order to solve these problems, a strategy that does not use recombinant proteins in the screening step has been developed, which is a strategy that uses cell surface proteins themselves for screening.

It has been found in conventional cited references that antibodies or peptides that bind directly to antigens expressed on the cell surface can be screened by incubating antibody candidates with the cells (Andersen P S, et al., Proc Natl Acad Sci USA 93:1820-1824, 1996; Barry M A, et al., Nat Med 2:299-305, 1995; Cai X, Garen A. Proc Natl Acad Sci USA 92:6537-6541, 1995).

However, the above-described cell-based display method has a disadvantage in that because screening is performed using cells cultured in the laboratory, the antibody screened by the method cannot properly exert its effect when actually applied to patients.

Meanwhile, an antibody-drug conjugate (ADC) is obtained by conjugating a cytotoxic drug to an antibody via a linker. Since a monoclonal antibody exhibits target specificity, the drug of the antibody-drug conjugate can be delivered to a tumor expressing an antigen/target which is recognized by a monoclonal antibody having selective targeting ability. Ideally, the antibody-drug conjugate which is maintained in a prodrug state in blood after administration should not be toxic, and as the antibody is internalized into cancer cells after binding to its target tumor antigen, the drug is released in an active form and kills tumor cells.

Thus, determining a target/antigen to which an antibody binds is an important starting point in the construction of antibody-drug conjugates. In particular, the target/antigen to which the antibody binds has become a cell surface protein predominantly expressed (overexpressed) in tumor cells.

The definition of antigens that are expressed on the surface of human cancer cells means a broad range of targets that are overexpressed relative to normal tissue or mutated and selectively expressed. The key problem is to identify appropriate antigens for antibody-based therapies. These therapeutic agents mediate changes in antigen or receptor function (i.e., function as stimulants or antagonists), regulate the immune system through Fc and T cell activation, and exert their efficacy by delivering a specific drug bound to an antibody that targets a specific antigen. Molecular technologies that can change antibody pharmacokinetics, function, size and immunostimulation properties have emerged as key elements in the development of new antibody-based therapies. Evidence obtained from clinical trials of therapeutic antibodies on cancer patients emphasizes the importance of approaches for the affinity and binding ability between target antigens and antibodies, the selection of antibody structures, and the selection of optimized antibodies, including therapeutic approaches (signaling inhibition or immune function).

Under these technical backgrounds, the inventors of the present application have made extensive efforts to develop an anticancer therapeutic antibody, which binds to NRP1 known to be expressed in various cancers and is internalized into cells. As a result, the present inventors have developed an anti-NRP1 antibody that binds with high affinity to NRP1 and is internalized into cells using phage display technology and have found that such an anti-NRP1 antibody can significantly inhibit the migration of cancer cells, thereby completing the present disclosure.

DISCLOSURE OF INVENTION

Technical Problem

An object of the present disclosure is to provide a method of screening an antibody using patient-derived tumor spheroids, which overexpress NRP1.

Another object of the present disclosure is to provide a method of screening an antibody using a patient-derived tumor spheroid overexpressing NRP1, and an animal model comprising the same.

Still another object of the present disclosure is to provide an antibody or an antigen-binding fragment thereof, which is screened by the method.

Yet another object of the present disclosure is to provide a composition for preventing or treating cancer, which comprises, as an active ingredient, the antibody or antigen-binding fragment thereof, which is screened by the method.

Technical Solution

To achieve the above object, the present disclosure provides a method for screening an antibody or an antigen-binding fragment thereof, which binds to NRP1, the method comprising the steps of: (i) treating patient-derived tumor spheroids, which express NRP1, with a library comprising antibodies or antigen-binding fragments thereof, and screening antibodies or antigen-binding fragments thereof which bind to NRP1; (ii) treating the screened antibodies or antigen-binding fragments thereof with patient-derived tumor spheroids that do not express NRP1; and (iii) separating or removing antibodies or antigen-binding fragments thereof, which bind to the patient-derived tumor spheroids of step (ii), from the antibodies or antigen-binding fragments thereof screened in step (i).

The present disclosure also provides a method for screening an antibody or an antigen-binding fragment thereof, which binds to NRP1, the method comprising the steps of: (i) treating patient-derived tumor spheroids, which express NRP1, with a library comprising antibodies or antigen-binding fragments thereof, and performing first screening of antibodies or antigen-binding fragments thereof which bind to NRP1; (ii) treating patient-derived tumor spheroids, which do not express the NRP1, with the first screened antibodies or antigen-binding fragments thereof; (iii) administering antibodies or antigen-binding fragments thereof, obtained by separating/removing antibodies or antigen-binding fragments thereof that binds to the patient-derived tumor spheroids of step (ii) from the antibodies or antigen-binding fragments thereof screened in step (i), to animal models transplanted with the patient-derived tumor spheroids which overexpress the NRP1, and performing second screening of antibodies or antigen-binding fragments which bind to NRP1; and (iv) separating or removing antibodies or antigen-binding fragments thereof, which bind to an antigen other than the NRP1, from the second screened antibodies or antigen-binding fragments thereof.

The present disclosure also provides an antibody or an antigen-binding fragment thereof, which is screened by the screening method.

The present disclosure also provides a composition for preventing or treating cancer, which comprises the antibody or the antigen-binding fragment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a conceptual view showing a method of the present disclosure.

FIG. 2 schematically shows a method of screening an antibody that binds to neuropilin 1 (NRP1) antigen, according to one embodiment of the present disclosure.

FIG. 3 schematically shows a method for in vivo screening of an antibody that binds to NRP1 antigen.

FIG. 4 shows the configuration of a phagemid vector for production of an anti-NRP1 antibody fragment according to one embodiment of the present disclosure, wherein the vector comprises the linker (GGGGS)$_3$ (SEQ ID NO: 1), as shown.

FIG. 5 shows the results of Coomassie staining of each anti-NRP1 antibody fragment purified according to one example of the present disclosure.

FIG. 6 shows the ELISA results indicating the binding affinities of three anti-NRP1 antibody fragments, screened according to one example of the present disclosure, for NRP1.

FIG. 7 shows the ELISA results indicating the binding affinities of three anti-NRP1 antibody fragments, screened according to one example of the present disclosure, according to NRP1 concentration.

FIG. 8 shows the results of SPR analysis performed to analyze the KD values of three anti-NRP1 antibody fragments, screened according to one example of the present disclosure.

FIG. 9 shows the FACS analysis results indicating the binding affinities of anti-NRP1 antibody fragments, screened according to one example of the present disclosure, for patient-derived tumor spheroids overexpressing NRP1.

FIGS. 10a to 10c are confocal laser scanning micrographs showing the internalizing function of three anti-NRP1 antibody fragments screened according to one example of the present disclosure.

FIG. 11 shows the results of confirming the binding epitope of anti-NRP1 antibody fragments screened according to one example of the present disclosure.

FIG. 12 shows the results of RNA-seq analysis performed to screen a cell line overexpressing NRP1.

FIG. 13 shows purity for three anti-NRP1 IgG antibodies.

FIG. 14 shows the results of an endotoxin test for three anti-NRP1 IgG antibodies.

FIG. 15 shows the results of measuring the KD values of anti-NRP1 IgG antibodies by ELISA.

FIG. 16 shows the specific binding affinities of three anti-NRP1 IgG antibodies for human NRP1.

FIG. 17 shows the results of confirming that three anti-NRP1 IgG antibodies screened according to a method of the present disclosure are internalized into patient-derived tumor spheroids.

FIG. 18 shows the results of confirming that three anti-NRP1 IgG antibodies screened according to a method of the present disclosure show cancer cell-specific internalization.

FIG. 19 shows the results of confirming that three anti-NRP1 IgG antibodies screened according to a method of the present disclosure show a higher difference between their binding affinities for normal cells and cancer cells than known NRP1 antibody.

FIG. 20 shows the results of confirming that three anti-NRP1 IgG antibodies screened according to a method of the present disclosure exhibit an excellent effect of inhibiting cancer cell migration.

FIG. 21 shows the results of confirming that an anti-NRP1 IgG antibody screened according to a method of the present disclosure exhibits an excellent effect of inhibiting cancer cell migration.

FIG. 22 shows the results of confirming the change in signaling substances by an anti-NRP1 IgG antibody screened according to a method of the present disclosure.

FIG. 23 shows the results of a TUNEL assay performed to confirm that apoptosis is increased by an anti-NRP1 IgG antibody screened according to a method of the present disclosure.

FIG. 24 shows the results of evaluating the efficacy of an anti-NRP1 IgG antibody, screened according to a method of the present disclosure, against glioblastoma.

FIG. 25 shows the results of evaluating the efficacy of an anti-NRP1 IgG antibody, screened according to a method of the present disclosure, against lung cancer.

FIG. 26 shows the results of confirming the glioblastoma-specific binding of an anti-NRP1 IgG antibody, screened according to a method of the present disclosure.

FIG. 27 shows the results of evaluating the distribution of an anti-NRP1 IgG antibody, screened according to a method of the present disclosure, in normal tissues.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well-known and commonly employed in the art.

In order to screen an antibody that has a high possibility of success in future clinical trials and can effectively act in cells after internalization, the present inventors have made extensive efforts to develop an anticancer therapeutic antibody using patient-derived tumor spheroids containing NRP1. As a result, the present inventors have screened an antibody that binds to NRP1 with high affinity and is internalized into cells using phage display technology, and have confirmed that such an antibody is internalized into cells.

Accordingly, in one example of the present disclosure, in order to screen an antibody which is internalized into cells by binding to NRP1 (neuropilin-1) known to be expressed in various cancers, phage display based on glioblastoma patient-derived tumor spheroids was performed. As a result, it was confirmed that the screened anti-NRP1 antibody was internalized into cells after binding to NRP1 expressed on the cancer cell surface (FIGS. 10a to 10c), and that the binding epitope of the antibody did differ from that of a conventional antibody (FIG. 11).

Therefore, in one aspect, the present disclosure is directed to a method for screening an antibody or an antigen-binding fragment thereof, which binds to NRP1, the method comprising the steps of: (i) treating patient-derived tumor spheroids, which express NRP1, with a library comprising antibodies or antigen-binding fragments thereof, and screening antibodies or antigen-binding fragments thereof which bind to NRP1; (ii) treating the screened antibodies or antigen-binding fragments thereof with patient-derived tumor spheroids that do not express NRP1; and (iii) separating or removing antibodies or antigen-binding fragments thereof, which bind to the patient-derived tumor spheroids of step (ii), from the antibodies or antigen-binding fragments thereof screened in step (i).

As used herein, the term "expression" means a process in which NRP1 is produced from a structural gene, and includes a process in which a gene is transcribed into mRNA which is then translated into an antigen. Generally, NRP1 can contribute to the creation of disease, for example, cancer, and may be overexpressed to inhibit the apoptosis of, for example, cancer cells, or overexpression of NRP1 can increase the invasiveness or migration of, for example, cancer cells. Thus, "expression of NRP1" in the method for screening the antibody or antigen-binding fragment thereof which binds to NRP1, according to the present disclosure, may be meant to include the overexpression or abnormal activation of NRP1.

As used herein, the term "antibody" is an immunoglobulin selected from the group consisting of IgA, IgE, IgM, IgD, IgY and IgG, which may bind specifically to a target antigen. The antibody is composed of two light chains and two heavy chains, and each of the chains is composed of a variable domain, which has a variable amino acid sequence, and a constant domain which has a constant amino acid sequence. At the end of the three-dimensional structure of the variable region, an antigen-binding domain is located. This antigen-binding domain is composed of complementarity determining regions, and each of the light and heavy chains comprises three complementarity determining regions. The complementarity determining regions have an especially high amino acid sequence variability among the variable domains. Due to this high variability, specific antibodies for various antigens can be found. The scope of the present disclosure also includes an intact antibody form as well as an antigen-binding fragment of the antibody molecule.

As used herein, the term "ScFv (single-chain Fv)" is an antibody consisting of light chain and heavy chain variable domains linked together. In some cases, the ScFv may comprise a linker consisting of peptide chains having about 15 amino acids linked together. In this case, the ScFv may have a structure of light chain variable domain-linker-heavy chain variable domain, or a structure of heavy chain variable domain-linker-light chain variable domain, and has antigen specificity equal or similar to that of the parent antibody.

The complete antibody is a structure having two full-length light chains and two full-length heavy chains, and each light chain is linked by a disulfide bond with a heavy chain. A constant region of the heavy chain has gamma (γ), mu (μ), alpha (α), delta (δ), and epsilon (ε) types. Subclasses have gamma 1 (γ1), gamma 2 (γ2), gamma 3 (γ3), gamma 4 (γ4), alpha 1 (α1), and alpha 2 (α2) types. A constant region of the light chain has kappa (κ) and lambda (λ) types.

An antigen-binding fragment or an antibody fragment of an antibody refers to a fragment having an antigen-binding function and includes Fab, F(ab'), F(ab')2, Fv, and the like. Fab of the antibody fragments has a structure including variable regions of a light chain and a heavy chain, a constant region of the light chain, and a first constant region (CH1) of the heavy chain with one antigen-binding site. Fab' differs from Fab in that it has a hinge region containing one or more cysteine residues at the C-terminal of the heavy chain CH1 domain. The F(ab')2 antibody is produced when the cysteine residue of the hinge region of the Fab' forms a disulfide bond. Recombinant techniques for generating Fv fragments with minimal antibody fragments having only a heavy chain variable region and a light chain variable region are described in PCT International Publication Nos. WO88/01649, WO88/06630, WO88/07085, WO88/07086, and WO88/09344. A two-chain Fv has a non-covalent bonding between a heavy chain variable region and a light chain variable region. A single chain Fv (scFv) is connected to a heavy chain variable region and a light chain variable region via a peptide linker by a covalent bond or directly at the C-terminal. Thus, the single chain Fv (scFv) has a structure such as a dimer like the two-chain Fv. Such an antibody fragment can be obtained using a protein hydrolyzing enzyme (for example, when the whole antibody is cleaved with papain, Fab can be obtained, and when whole antibody is cut with pepsin, F(ab')2 fragment can be obtained), and it can also be produced through gene recombinant technology.

As used herein, the term "antibody (or ScFv) library" is a collection of various antibody genes having different sequences. To separate an antibody specific for any antigen from an antibody library, a very high diversity is required. A library consisting of different antibody clones is constructed and used. The antibody gene of this antibody library may be cloned into, for example, a phagemid vector, and transformed into a host cell (*E. coli*).

As used herein, the term "nucleic acid" may be used interchangeably with the term "gene" or "nucleotide". For example, the nucleic acid may be selected from the group consisting of natural/synthetic DNA, genomic DNA, natural/synthetic RNA, cDNA and cRNA, but is not limited thereto.

As used herein, the term "phagemid" vector is a plasmid DNA which is used in phage display and has a phage origin of replication. It generally has an antibiotic resistance gene as a selection marker. A phagemid vector that is used in phage display includes the gIII gene of M13 phage or a portion thereof, and the ScFv gene is ligated to the 5' end of the gIII gene and expressed in a host cell.

As used herein, the term "helper phage" is a phage that provides necessary genetic information so that phagemid is packaged into phage particles. Since phagemid includes the gIII gene of phage or a portion thereof, a host cell (transformant) transformed with the phagemid is infected with the helper phage to provide the remaining phage gene. The helper phages include M13K07 or VCSM13, and mostly include an antibiotic resistance gene such as a kanamycin resistance gene so that a transformant infected with the helper phage can be selected. In addition, the packaging signal is defective, and thus the phagemid gene rather than the helper phage gene is selectively packaged into phage particles.

As used herein, the term "signal sequence" is either a nucleotide sequence which is located at the 5'end of the gene and functions as a necessary signal when a protein encoded by the gene is secreted extracellularly, or an amino acid sequence corresponding thereto.

As used herein, the term "Phage display" refers to a technique that displays a fusion protein by fusing a mutant polypeptide and at least a part of a coat protein on a surface of phase, for example, a fibrous phage particle. The phage display is useful for targeting a large library of randomized protein variants to quickly and efficiently classify sequences that bind to target antigens with high affinity. Displaying peptides and protein libraries on phage has been used to screen millions of polypeptides to identify polypeptides with specific binding properties.

The phage display technique has provided a powerful tool for generating and screening novel proteins that bind to specific ligands (e.g., antigens). Using the phage display technique, a large library of protein variants can be generated and sequences binding to the target antigens with high affinity can be rapidly classified. The nucleic acid encoding the mutant polypeptide is fused with a nucleic acid sequence encoding a viral coat protein, e.g., a gene III protein or a gene VIII protein. A monovalent phage display system has been developed in which a nucleic acid sequence encoding a protein or polypeptide is fused with a nucleic acid sequence encoding a part of the gene III protein. In the monovalent phage display system, the gene fusion is expressed at a low level, and the wild-type gene III protein is also expressed, thereby maintaining the infectivity of the particles.

Demonstrating the expression of peptides on the fibrous phage surface and the expression of functional antibody fragments in the peripheral cytoplasm of a host cell is important in developing antibody phage display libraries. Libraries of antibodies or antigen-binding polypeptides have been prepared in a number of ways, for example by altering a single gene by inserting a random DNA sequence or by cloning a related genic line. The library can be screened for expression of antibodies or antigen binding proteins with the desired characteristics.

The phage display technique has several advantages over conventional hybridomas and recombinant methods for producing antibodies with the desired characteristics. This technique allows the generation of a large antibody library having various sequences in a short time without the use of animals. The production of hybridomas or humanized antibodies may take several months to manufacture. Further, the phage antibody library may produce antibodies against antigens that are toxic or have low antigenicity since no immunity is required. The phage antibody library can also be used to generate and identify novel therapeutic antibodies.

A technology can be used in which human antibodies are generated from virgin B-cell Ig repertoires or human germline sequences immunized or non-immunized using a phage display library. Various lymphatic tissues may be used to prepare virgin or non-immune antigen-binding libraries.

Techniques for identifying and separating high affinity antibodies from a phage display library are important for separating new therapeutic antibodies. The separation of high affinity antibodies from the library may depend on the size of the library, production efficiency in bacterial cells, and library diversity. The size of the library is reduced by inefficient production due to improper folding of an antibody or antigen binding protein and the presence of the stop codon. Expression in bacterial cells can be inhibited when an antibody or antigen binding domain is not properly folded. The expression can be increased by alternately mutating residues on a surface of a variable/constant interface or selected CDR residues. A sequence of the framework region is one element to provide appropriate folding when antibody phage libraries are generated in bacterial cells.

It is important to generate various libraries of an antibody or antigen binding proteins in high affinity antibody separation. The CDR3 region has been found to often participate in antigen binding. The CDR3 region on a heavy chain varies considerably in terms of size, sequence, and structural steric conformation so that various libraries can be prepared using the CDR3 region.

Further, diversity may be generated by randomizing the CDR regions of the variable heavy and light chains using all amino acids at each position. The use of all 20 amino acids results in an increased variability of variant antibody sequences and an increased chance of identifying new antibodies.

As used herein, the term "neuropilin" or "NRP" collectively includes neuropilin-1 (NRP1), neuropilin-2 (NRP2), and their isoforms and variants. Neuropilins are 120-130 kDa non-tyrosine kinase receptors. There are multiple NRP-1 and NRP-2 splice variants and soluble isoforms. The basic structure of neuropilins comprises five domains: three extracellular domains (ala2, b1b2 and c), a transmembrane domain, and a cytoplasmic domain. The ala2 domain is homologous to complement components Clr and Cls (CUB), which generally contains four cysteine residues that form two disulfide bridges. The b1b2 domain is homologous to coagulation factors V and VIII. The central portion of the c domain is designated as MAM due to its homology to meprin, AS and receptor tyrosine phosphotase µ proteins. The ala2 and b1b2 domains are responsible for ligand binding, whereas the c domain is critical for homodimerization or heterodimerization.

"Neuropilin-mediated biological activity" refers to physiological or pathological events in which neuropilin-1 plays a substantial role. For example, such activities may be axon guidance during embryonic nervous system development or neuron-regeneration, angiogenesis (including vascular modeling), tumorgenesis and tumor metastasis, but are not limited thereto.

The antibody of the present disclosure includes monoclonal antibodies, multispecific antibodies, human antibodies, humanized antibodies, chimeric antibodies, and the like, but is not limited thereto. The antibody of the present disclosure includes an antigen-binding fragment of the antibody or an antibody fragment, and the fragment may include single-chain Fvs (scFV), single chain antibodies, Fab fragments, F(ab') fragments, disulfide-linked Fvs (sdFV), and anti-idiotype (anti-Id) antibodies.

The monoclonal antibody refers to an antibody obtained from a substantially homogeneous population of antibodies, i.e., the same except for possible naturally occurring mutations that may be present in trace amounts of individual antibodies that occupy the population. The monoclonal antibody is highly specific and is derived against a single antigenic site.

The non-human (e.g. murine) antibody of the "humanized" form is a chimeric antibody containing minimal sequence derived from non-human immunoglobulin. In most cases, the humanized antibody is a human immunoglobulin (receptor antibody) that has been replaced by a residue from the hypervariable region of a non-human species (donor antibody), such as a mouse, rat, rabbit, and non-human primate, having specificity, affinity, and ability to retain a residue from the hypervariable region of the receptor.

"Human antibody" is a molecule derived from human immunoglobulin and means that all of the amino acid sequences constituting the antibody including the complementarity determining region and the structural region are composed of human immunoglobulin.

A heavy chain and/or light chain is partly identical or homologous to the corresponding sequence in an antibody derived from a particular species or belonging to a particular antibody class or subclass, while the remaining chain(s) are identical or homologous to corresponding sequences in an antibody derived from another species or belonging to another antibody class or subclass "chimeric" antibodies (immunoglobulins) as well as a fragment of such antibody exhibiting the desired biological activity.

"Antibody variable domain" as used herein refers to the light and heavy chain regions of an antibody molecule including the amino acid sequences of a complementarity determining region (CDR; i.e., CDR1, CDR2, and CDR3) and a framework region (FR). VH refers to a variable domain of the heavy chain. VL refers to a variable domain of the light chain.

"Complementarity determining region" (CDR; i.e., CDR1, CDR2, and CDR3) refers to the amino acid residue of the antibody variable domain, which is necessary for antigen binding. Each variable domain typically has three CDR regions identified as CDR1, CDR2, and CDR3.

"Framework region" (FR) is a variable domain residue other than a CDR residue. Each variable domain typically has four FRs identified as FR1, FR2, FR3, and FR4.

The method of the present disclosure comprises step (i) of treating patient-derived tumor spheroids, which express NRP1, with a library comprising antibodies or antigen-binding fragments thereof, and screening antibodies or antigen-binding fragments thereof which bind to NRP1.

The patient-derived tumor spheroids may be, for example, cancer patient-derived tumor spheroids, and cancer patient-derived tumor spheroids exhibit physiological characteristics different from those of normal cells. Such physiological characteristics are determined by a gene expression pattern in which the expression of the antigen increases or decreases specifically in cancer cells compared to normal cells. This gene expression pattern may be patient-specific, or may show a patient's tissue-specific difference.

A method for measuring the antigen contents of the patient-derived tumor spheroids and normal cells may comprise measuring and comparing the expression level of a gene or protein encoding the antigen. Preferably, the method may be performed by any one method selected from the group consisting of FACS, ELISA, whole exome sequencing, and RNA sequencing, but is not limited thereto.

In the present disclosure, the patient-derived tumor spheroid may be derived from a solid cancer patient, and the solid cancer may be selected from the group consisting of liver cancer, glioblastoma, ovarian cancer, colon cancer, head and neck cancer, bladder cancer, renal cell cancer, breast cancer, metastatic cancer, prostate cancer, pancreatic cancer, and lung cancer, but is not limited thereto.

A method for obtaining the patient-derived tumor spheroids is not particularly limited, and may, for example, comprise the steps of: (a) dissociating isolated cancer patient-derived cancer tissue, and collecting a cell fraction from the dissociated tissue; and (b) treating the collected cell fraction with protease, followed by filtration, centrifugation and suspension, thereby obtaining single cells.

In the present disclosure, the protease may be an enzyme capable of performing proteolysis, and examples thereof may include: endopeptidase that degrades a protein by protein catabolism that hydrolyzes a peptide bond connecting amino acids in the protein; and exopeptidase that hydrolyzes a peptide bond from the N-terminus or C-terminus of a protein.

The method of the present disclosure also comprises step (ii) of incubating the screened antibodies or antigen-binding fragments thereof with patient-derived tumor spheroids that do not express NRP1.

Step (ii) is a step of performing negative selection on the antibodies or antigen-binding fragments thereof screened in step (i). The method of the present disclosure also comprises step (iii) of separating or removing antibodies or antigen-binding fragments thereof, which bind to the patient-derived tumor spheroids of (ii), from the antibodies or antigen-binding fragments thereof screened in (i). By virtue of this step, an antibody having high selectivity for an antigen can be screened.

In the present disclosure, the patient-derived tumor spheroids which does not express NRP1, which are used in step (ii), may be cells that do not naturally express NRP1, or patient-derived tumor spheroids artificially engineered so as not to express NRP1. A method for artificially engineering the cells may be any method that prevents NRP1 from being expressed. Preferably, the patient-derived tumor spheroids that do not express NRP1 may be obtained by treatment with one or more selected from the group consisting of aptamers, siRNA, single-stranded siRNA, microRNA, and shRNA, which bind to NRP1.

In the present disclosure, the step of screening only an antibody, which binds to NRP1, by use of the patient-derived tumor spheroids that do not express NRP1, is a negative selection step which is performed following the immediately preceding positive selection step, and thus has the effect of increasing the accuracy of the screened antibody for NRP1.

In some cases, the method of the present disclosure may further comprise, during or after step (ii), a step of performing phage display at 4° C., and then screening an antibody, which is internalized into the cells, at an increased temperature of 37° C. By virtue of this step, the antibody internalized into the cells can be screened.

The separating or removing of the antibodies or antigen-binding fragments thereof may be performed by using electrophoresis, centrifugation, gel filtration, precipitation, dialysis, chromatography (including ion exchange chromatography, affinity chromatography, immunoadsorption chromatography, size exclusion chromatography, and the like), isoelectric focusing, and variations and combinations thereof, but is not limited thereto.

The separating or removing of the antibodies or antigen-binding fragments thereof may be performed by removing impurities by, for example, centrifugation or ultrafiltration, and purifying the resulting product by using, for example, affinity chromatography and the like. Other additional purification techniques, for example, anion or cation exchange chromatography, hydrophobic interaction chromatography, hydroxylapatite chromatography, and the like may be used.

In another aspect, the present disclosure is directed to a method for screening an antibody or an antigen-binding fragment thereof, which binds to NRP1, the method comprising the steps of: (i) treating patient-derived tumor spheroids, which express NRP1, with a library comprising antibodies or antigen-binding fragments thereof, and performing first screening of antibodies or antigen-binding fragments thereof which bind to NRP1; (ii) treating patient-derived tumor spheroids, which do not express the NRP1, with the first screened antibodies or antigen-binding fragments thereof; (iii) administering antibodies or antigen-binding fragments thereof, obtained by separating or removing antibodies or antigen-binding fragments thereof that binds to the patient-derived tumor spheroids of step (ii) from the antibodies or antigen-binding fragments thereof screened in step (i), to animal models transplanted with the patient-derived tumor spheroids which overexpress the NRP1, and performing second screening of antibodies or antigen-binding fragments which bind to NRP1; and (iv) separating or removing antibodies or antigen-binding fragments thereof, which bind to an antigen other than the NRP1, from the second screened antibodies or antigen-binding fragments thereof.

The description of the same configuration as that described in the above-described screening method can be applied equally.

In another example of the present disclosure, in order to screen an antibody which is internalized into cells by binding to NRP1 (neuropilin-1) known to be expressed in various cancers, phage display based on glioblastoma patient-derived tumor spheroids was performed, and then the first screened antibody candidates were injected into immunodeficient mice including the patient-derived tumor spheroids, and second screening in vivo was performed. As a result, it was confirmed that the screened anti-NRP1 antibody was internalized into cells after binding to NRP1 expressed on the cancer cell surface (FIGS. 10a to 10c), and that the binding epitope of the antibody did differ from that of a conventional antibody (FIG. 11).

In particular, the method of the present disclosure further comprises a step of administering antibodies or antigen-binding fragments thereof, obtained by separating or removing antibodies or antigen-binding fragments thereof that binds to the patient-derived tumor spheroids of step (ii) from the antibodies or antigen-binding fragments thereof screened in step (i), to animal models transplanted with the patient-derived tumor spheroids which overexpress the NRP1, and performing second screening of antibodies or antigen-binding fragments which bind to NRP1.

The screening method comprising the above-described steps according to the present disclosure makes it possible to sufficiently reflect the characteristics of patients through animal models transplanted with patient-derived tumor spheroids overexpressing NRP1. Thus, it may be used for the screening of a patient-specific therapeutic drug and the selection of a treatment method, and can also screen an antibody or an antigen-binding fragment thereof, which is particularly suitable for patient characteristics, with high accuracy.

In the present disclosure, the animal models transplanted with patient-derived tumor spheroids overexpressing NRP1 may be any animals including the patient-derived tumor spheroids. Preferably, the animal models may be immunodeficient mice. The "immunodeficient mice" refer to mice generated by artificially damaging some elements of the immune system at the gene level such that the immune system becomes abnormal and glioblastoma can develop. Most preferably, the immunodeficient mice may be nude mice, NOD (non-obese diabetic) mice, SCID (Severe combined immunodeficiency) mice, NOD-SCID mice, or NOG (NOD/SCID I12rg-/-) mice.

The method according to the present disclosure can screen, for example, an antibody that binds to NRP1 overexpressed in patient-derived tumor spheroids, but is not limited thereto. The antibody may be, for example, an antibody that binds to the VEGF165 domain of NRP1, but the binding epitope of this antibody may differ from that of a conventional antibody (antibody MNRP1685A, Genetech) known to bind to the VEGF165 domain of NRP1.

The antibody or antigen-binding fragment thereof screened by the method according to the present disclosure may be, for example, an IgG format, an Fab' fragment, an F(ab')2 fragment, an Fab fragment, an Fv fragment, or a single-chain Fv (scFv) fragment. Preferably, it may be converted to an IgG format.

In still another aspect, the present disclosure is directed to an antibody or an antigen-binding fragment thereof, which is screened by the method.

An antibody or antibody fragment of the present disclosure may include, within the scope of specifically recognizing NRP1, the sequence of the anti-NRP1 antibody of the present disclosure described herein as well as biological equivalents thereof. The amino acid sequence of the antibody may be additionally modified to further improve the binding affinity and/or other biological properties of the antibody. Such modifications include, for example, deletion, insertion and/or substitution of the amino acid sequence residues of the antibody. Such amino acid variations are made based on the relative similarity of amino acid side chain substituents, such as hydrophobicity, hydrophilicity, charge, and size. By analysis of the size, shape and type of amino acid side chain substituents, it is recognized that each of arginine, lysine and histidine is a positively charged residue; alanine, glycine and serine have similar sizes; and phenylalanine, tryptophan and tyrosine have similar shapes. Based on these considerations, it is thus found that arginine, lysine and histidine; alanine, glycine and serine; and phenylalanine, tryptophan and tyrosine, respectively, are biologically functional equivalents.

In introduction of mutations, the hydropathic index of amino acids can be considered. Each amino acid is assigned a hydrophobic index according to its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in imparting the interactive biological function of proteins. It is well known that substitution with an amino acid having a similar hydrophobic index can retain similar biological activities. When a mutation is introduced with reference to a hydrophobic index, the substitution is made between amino acids showing a hydrophobic index difference preferably within ±2, more preferably within ±1, even more preferably within ±0.5.

Meanwhile, it is also well known that the substitution between amino acids with similar hydrophilicity values leads to proteins with equivalent biological activity. As disclosed in U.S. Pat. No. 4,554,101, the following hydrophilicity values are assigned to each amino acid residue: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Amino acid substitution in proteins that do not totally alter the activity of the molecule is known in the art. The substitution occurs the most commonly between amino acid residues, e.g., Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

Considering the mutation having the above-mentioned biological equivalent activity, the antibody of the present disclosure or the nucleic acid molecule encoding the same is interpreted to include a sequence showing substantial identity with the sequence described in the sequence listing. The substantial identity means a sequence showing at least 61% homology, more preferably 70% homology, even more preferably 80% homology, and most preferably 90% homology by aligning the sequence of the present disclosure with any other sequence as much as possible and analyzing the aligned sequence using algorithms commonly used in the art. Alignment methods for sequence comparison are well known in the art. NCBI Basic Local Alignment Search Tool (BLAST) may be accessible from, e.g., NBCI and can be used in association with sequence analysis programs such as blastp, blasm, blastx, tblastn and tblastx on the Internet. BLSAT is available at https://blast.ncbi.nlm.nih.gov/Blast.cgi. A comparison of sequence homology using this program can be found at https://blast.ncbi.nlm.nih.gov/Blast.cgi.

In the present disclosure, the antibody or antigen-binding fragment thereof may bind to an antigen, for example, an antigen involved in development, growth and migration of cancer or tumor. Form of the antigen may be, for example, in the form of oligomer, peptide, polypeptide or protein.

In one example of the present disclosure, the present disclosure may provide a method for screening an antibody or an antigen-binding fragment thereof, which binds specifically to NRP1.

In yet another aspect, the present disclosure is directed to a composition for preventing or treating cancer, which comprises the antibody or antigen-binding fragment thereof as an active ingredient.

The present disclosure may be, for example, a pharmaceutical composition for preventing or treating cancer, comprising (a) a pharmaceutical effective amount of an antibody or antigen-binding fragment thereof against NRP1 according to the present disclosure; and (b) a pharmaceutically acceptable carrier. The present disclosure is also directed to a method for prevention or treatment of cancer, comprising administering an effective amount of an antibody or antigen-binding fragment thereof against NRP1 according to the present disclosure to a patient.

Since the composition uses the anti-NRP1 antibody or antigen-binding fragment thereof of the present disclosure as an active ingredient, the descriptions common to both of them are excluded in order to avoid the excessive complexity of the present specification caused by the repeated descriptions.

As demonstrated in Examples as described below, the anti-NRP1 antibody of the present disclosure can inhibit the migration of cancer cells overexpressing NRP1. As such, the antibody and antigen-binding fragment thereof of the present disclosure binds to NRP1 with high affinity and thus inhibits the migration of cancer cells overexpressing NRP1, so that it can be used in the prevention and treatment of a cancer.

In one example of the present disclosure, it was confirmed that the anti-NRP1 antibody screened by the method of the present disclosure could show cancer cell-specific internalization (Example 9), and could exhibit the effect of increasing apoptosis and a desired tumor growth inhibitory effect in solid cancers, for example, glioblastoma and lung cancer (Example 11). In particular, it was confirmed that the anti-NRP1 antibody screened by the method of the present disclosure had little or no binding affinity for normal tissue, suggesting that the side effects of the antibody can be minimized (Example 12).

As used herein, the term "prevention" means any action that inhibits or delays progress of a cancer by administration of a composition according to the present disclosure, and "treatment" means suppression of development, alleviation, or elimination of a cancer.

The composition is applied to a disease that is a cancer overexpressing NRP1, for examples, glioblastoma, astrocytoma, glioma, neuroblastoma, testicular cancer, colon cancer, melanoma, pancreatic cancer, lung cancer, breast cancer, esophageal cancer, and prostate cancer.

As used herein, the term "cancer overexpressing EGFRvIII" refers to a cancer having EGFRvIII on the cancer cell surface at a significantly higher level compared to non-cancerous cells of the same tissue type.

A pharmaceutically acceptable carrier to be contained in the composition of the present disclosure is conventionally used in the formulation and includes, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, water, syrup, methylcellulose, methylhydroxybenzoate, propylhydroxybenzoate, talc, magnesium stearate, mineral oil, and the like. The composition of the present disclosure may further include, e.g., a lubricant, a wetting agent, a sweetener, a flavoring agent, an emulsifying agent, a suspending agent, and a preservative in addition to the components.

The pharmaceutical composition of the present disclosure may be administered orally or parenterally. The parenteral administration is carried out by intravenous injection, subcutaneous injection, intramuscular injection, intraperitoneal injection, endothelial administration, topical administration, intranasal administration, intrapulmonary administration, rectal administration, and the like.

Because a protein or peptide is digested when administered orally, a composition for oral administration should be formulated to coat or protect an active drug agent against degradation in stomach. Also, the pharmaceutical composition may be administered by any device which can transport active substances to target cells.

The appropriate dosage of the composition according to the present disclosure may vary depending on factors such as the formulation method, the administration method, patient's age, body weight, sex, pathological condition, food, administration time, route of administration, excretion rate and reaction sensitivity. Thus, a commonly skilled physician can easily determine and prescribe a dosage that is effective for the desired treatment or prophylaxis. For example, the daily dosage of the pharmaceutical composition of the present disclosure is 0.0001 mg/kg to 100 mg/kg. The term "pharmaceutically effective amount" as used herein refers to an amount sufficient to prevent or treat cancer.

The pharmaceutical composition of the present disclosure may be formulated using a pharmaceutically acceptable carrier and/or an excipient according to a method which can be easily carried out by those having ordinary skill in the art to which the present disclosure pertains so as to be provided in a unit dosage form or enclosed into a multi-dose container. Here, the formulations may be in the form of solutions, suspensions or emulsions in oils or aqueous media, or in the form of extracts, grains, suppositories, powders, granules, tablets or capsules, and may additionally include dispersing or stabilizing agents.

The composition of the present disclosure may be administered as an individual therapeutic agent or in combination with another therapeutic agent, and may be administered sequentially or simultaneously with a conventional therapeutic agent.

EXAMPLES

Hereinafter, the present disclosure will be described in further detail with reference to examples. It will be obvious to a person having ordinary skill in the art that these examples are for illustrative purposes only and are not to be construed to limit the scope of the present disclosure.

Example 1: First Identification of Internalizing Antibodies Using Patient-Derived Tumor Spheroids To screen cells required for cell panning for identification of anti-NRP1 antibody fragments, the NRP1 expression levels of patient-derived tumor spheroids obtained from the Institute for Refractory Cancer Research at Samsung Medical Center were analyzed by RNA-Seq followed by RPKM (Reads Per Killobase Million) method (FIG. 12), and cells with high expression level of NRP1 were selected by FACS (Fluorescence Activated Cell Sorting) method and used in cell panning.

scFv antibody fragments that bind to human NRP1 were identified by phage display screening using the previously prepared synthetic scFv antibody fragment phage library (Yang et al., Mol. Cells. 27:225-235, 2009). Each of four sub-library samples was cultured in 400 ml culture medium (SB/ampicillin/2% glucose) for two hours to recover the phagemid vector introduced into *Escherichia coli* host cell ER2537 in a phage form. When the absorbance at O.D. 600 reached about 0.5 to 0.7, the supernatant was removed by centrifugation at 5000 g for 20 minutes, and then the cells were suspended in 400 ml of a secondary culture medium (SB/ampicillin). Then, $10^{12}$ pfu (plaque forming unit) of a helper phage (VCSM13) was added to the cells and incubated for one hour. Next, 70 μg/ml of kanamycin antibiotic (an antibiotic gene introduced in helper phage) was added and incubated overnight at 30° C. to allow the phage library to be secreted out of the host cells. Then, the culture obtained by centrifugation was precipitated only in the form of phage using polyethylene glycol (PEG) solution, thereby obtaining a phage library.

The phage library obtained as described above and patient-derived tumor spheroids ($4 \times 10^6$) with high NRP1 expression were mixed, added to a total of 5 ml of NBA (neurobasal medium), fixed in a rotator at 4° C., and then rotated 360 degrees for 1 to 2 hours. Then, the cells were centrifuged at 300 g for 5 minutes to remove the phage particles that did not bind to the patient-derived tumor spheroids, and then the cells were washed again by adding 5 ml of NBA. This procedure was repeated four times. In the final step, patient-derived tumor spheroids and phages were placed in a T flask using 5 ml of NBA placed in an incubator at 37° C., and were incubated for 30 minutes at 37° C. to induce the phage particles attached to the cell surface to enter the cells by internalization.

Then, the cell solution was placed in a 15-ml conical tube, and the cells were separated by centrifugation at 300 g for 5 minutes, and then washed with 5 ml of cold PBS (phosphate buffered saline). The washing process was repeated 6 times. The number of these processes was increased as the number of the cell panning increased. Then, 5 ml of 0.1 M glycine (pH 2.2) was added, and the mixture was kept at room temperature for 5 minutes to separate the cell surface-attached phage particles from the cell surface. Then, the cells were separated by centrifugation at 300 g for 5 minutes, and 0.5 ml of 100 mM TEA was added thereto. The cells were transferred to an e-tube and left at room temperature for 15 minutes. Next, the cell debris was separated by centrifugation at 12,000 rpm for 5 minutes, and the supernatant containing the phage particles in the cells was collected and neutralized by mixing with 1 ml of 2M Tris (pH 8). Thereafter, the neutralized supernatant was placed in 8.5 ml of a culture medium (SB) containing pre-grown ER2537, and incubated at 37° C. at 120 rpm to infect *Escherichia coli* host cell ER2537 with the phage particles. Thereafter, the culture medium was centrifuged at 3,000 rpm for 15 minutes, and the precipitated ER2537 was mixed with 500 μl of a culture medium (SB), followed by spreading on a 15 cm culture medium. After culturing, 5 ml of SB culture medium (50% glycerol) was added thereto, and the colonies were collected and stored (−80° C.) To proceed with repeated cell panning, 1 ml of the stored phage solution from the previous round of panning was taken and subjected to phage particle amplification. After incubation in host cell ER2537, the helper phage was added, and the recovered phage particles were separated by PEG precipitation. These particles were used for the next round of panning in the same manner. The third round of panning was performed, and the cell panning procedure is shown in FIG. 2. It was confirmed that the ratio of the phage particles after the panning to those before the panning was increased as the number of panning rounds increased. This means that the internalized phage particles were amplified through cell panning. The results are shown in Table 1 below.

TABLE 1

Cell panning using patient-derived tumor spheroids

| | Input | Wash | Output | Out/Input |
|---|---|---|---|---|
| 1 round | $1.1 * 10^{13}$ | $2.2 * 10^4$ | $2.7 * 10^3$ | $2.5/10^{10}$ |
| 2 round | $2.5 * 10^{13}$ | $5.0 * 10^3$ | $1.32 * 10^5$ | $5.28/10^9$ |
| 3 round | $1.5 * 10^{13}$ | $3.1 * 10^4$ | $1.49 * 10^6$ | $9.93/10^7$ |

Example 2: ELISA and Sequencing for Screening of Anti-NRP1 Antibody Fragment Candidates The phage particles recovered from the 3rd round cell panning were confirmed as colonies in the medium through host cell (ER2537) infection. These colonies were taken, inoculated into 96-well plates containing 200 μl of SB/ampicillin medium, and then incubated for 2 to 3 hours at 37° C.

Then, each well was treated with IPTG (isopropyl beta-D-1-thiogalactopyranoside) at a final concentration of 1 mM for induction of scFv-pIII protein expression and incubated overnight at 30° C. The incubated plate was centrifuged at 3,000 rpm for 15 minutes, and the supernatant was removed. Thereafter, in order to recover the phage particles from the periplasm of the incubated cells, 40 μl of TES solution (20% w/v sucrose, 50 mM Tris, 1 mM EDTA, pH 8.0) was added to each well and left at 4° C. for 30 minutes so as to lyse the cells. Then, the cells were treated with 60 μl of 0.2×TES solution and incubated at 4° C. for 30 minutes to disrupt the cells by osmotic pressure. Then, the plate was centrifuged at 3,000 rpm for 15 minutes, and the supernatant scFv-pIII protein was obtained.

25 μl of the obtained supernatant was added to each of a 96-well plate coated with previously prepared human NRP1 protein, and then incubated at room temperature for 1 hour, and each well was washed six times with TBST and distilled water. Then, each well was incubated with HRP-conjugated anti-HA antibody capable of binding to the HA tag of scFv-pIII for 1 hour at room temperature, and then washed six times with TBST (0.1% Tween 20) and distilled water. TMB solution was used to induce the color reaction. The color reaction was stopped with $H_2SO_4$ solution, and the absorbance at 450 nm OD was measured.

The total number of clones analyzed was 384, of which 41 clones (binding affinity >2-fold) showed high binding affinity for human NRP1. As a control, BSA solution was used. Among the 41 clones, 10 clones with high binding affinity were selected by ELISA. Then, the phagemid was recovered from 10 clones and subjected to DNA sequencing, and a total of six clones having different sequences were selected. Clones having different sequences were selected except for 3H10 having the same sequence as that of 1C08, and finally 3H10, 1A03 and 4F12 clones were selected as anti-NRP1 antibody fragment candidates. The amino acid sequences of the 3H10, 1A03 and 4F12 clones are shown in Tables 2 and 3 below.

TABLE 2

Heavy-chain FR/CDR sequences of anti-NRP1 antibody fragments

| | FR1 | CDR1 | FR2 | CDR2 | FR3 | CDR3 | FR4 |
|---|---|---|---|---|---|---|---|
| 1A03 | EVQLLES GGGLVQF GGSLRLS QAAS | GFTF SSYY | MSWVRQA FGKGLEW VSA | ISFG SSNK | YYADSVQGRFTI SRDNSKNTLYLQ MNELRAEDTAVY YC | ARRK KSFD Y | WGQGT LVTVS S |
| 3H10 | EVQLLES GGGLVQF QQSLRLS QAAS | QFTF SSYY | MSWVRQA FGKGLEW VSA | ISPG SSNK | YYADSVKGRFTI SRDNSKNTLYLQ MNELRAEDTAVY YC | ARRK YMFD Y | WGQGT LVTVS S |
| 4F12 | EVQLLES GGGLVQF GGSLRLS QAAS | GFTF SGYA | MSWVRQA FGKGLEW VSG | ISPG SGST | YYADSVKGRFTI SRDNEKNTLYLQ MNELRAEDTAVY YC | AKRK TRFD Y | WGQGT LVTVS S |

TABLE 3

Light-chain FR/CDR sequences of anti-NRP1 antibody fragments

| | FR1 | CDR1 | FR2 | CDR2 | FR3 | CDR3 | FR4 |
|---|---|---|---|---|---|---|---|
| 1A03 | QSVLTQFF SASGTPGQ RVTISCSG F | SSNI GNND | VSWYQQ LFGTAP KLLIY | SCN | NRPSGVPDRF SGSKSGTSAS LAISGLRSSD EADYYC | GAWV ASLS AYV | FGGGTK LTVTL |
| 3H10 | GSVLTQPP SASGTPGQ RVTISCTG E | SSNI GNND | VYWYQQ LPGTAF KLLIY | SQS | NRPSGMPDRF SGSKSGTSAS LAISGLRSED EADYYC | ASWD SSLS GYV | FGGGTK LTVTL |
| 4F12 | QSVLTQFF SASGTFGR RVTISQSG S | SSNI GNNE | VYWYQQ LPGTAP KLLIY | ANN | KRFSGMPDRF SGSKEGTSAS LAISGLRSED EADYYC | AAWD SSLN GYV | FGGGTK LTVTL |

Example 3: Second Identification of Internalizing Antibodies Using Patient-Derived Tumor Spheroids The candidate antibodies recovered from the 3rd cell panning in Example were intratumorally injected into mice transplanted subcutaneously with the patient-derived tumor spheroids used in Example 1.

After 20 hours, the mice were sacrificed, and the cancer tissue was dissociated into single cells. Then, the antibody fragments internalized in the cancer cells were recovered and analyzed by ELISA in the same manner as described in Example 2.

This in vivo cell panning procedure is shown in FIG. 3. It was confirmed that the ratio of the phage particles after the panning to those before the panning was increased as the number of panning rounds increased. This means that the internalized phage particles were amplified through cell panning. The results are shown in Table 4 below (unit: cfu/ml).

TABLE 4

| | Input | Binding & no-internalization | Output | Output/Input |
|---|---|---|---|---|
| 1 round | $2.4 * 10^{13}$ | $3 * 10^6$ | $8 * 10^4$ | $3.3/10^9$ |
| 2 round | $3.5 * 10^{15}$ | $1.8 * 10^7$ | $1.2 * 10^5$ | $3.4/10^{11}$ |
| 3 round | $2.5 * 10^{15}$ | $2.0 * 10^8$ | $2.4 * 10^5$ | $9.6/10^9$ |

Example 4: Production of Anti-NRP1 Antibody Fragments and Analysis of Binding Affinity for NRP1

The basic structure of phagemid is shown in FIG. 4. In the case of the host cell ER2537 used in the above examples, scFv cannot be expressed alone because the transcriptional suppression codon (amber codon (UAG)) located upstream of phage pIII is suppressed. Therefore, using an expression strain (TOP10F') which is a non-suppressor strain, the phagemid was transfected into the expression strain. Thereafter, through DNA sequencing, it was confirmed that the expression strain was an expression strain in which each phagemid was introduced without mutation. The expression strain was taken as a colony, inoculated into 3 ml of LB/ampicillin medium, and then cultured overnight at 37° C. Thereafter, 3 ml of the overnight culture was transferred to 400 ml of medium (SB/ampicillin) and cultured until the OD 600 reached 0.5 to 0.7. IPTG was added thereto to a final concentration of 1 mM, followed by culture overnight at 30° C. After the culture was centrifuged, 40 ml of TES solution was used to lyse the expression host, and then 60 ml of 0.2×TES was added and the phage particles in the periplasm were recovered. The recovered supernatant was filtered through a 0.45 μm filter. The scFv protein present in the filtered solution was added to 1 ml of Ni-NTA bead (Qiagen) for His-tag purification and bound for 1 hour at room temperature. Thereafter, the resulting material was packed in a gravity column (Bio-rad) and recovered via 200 mM imidazole solution. After the expression and purification of each clone, it was confirmed through SDS-PAGE and Coomassie blue staining that the size of scFv was about 28 kDa (FIG. 5).

Whether the purified scFv would have binding affinity for the target NRP1 was analyzed by ELISA. In a 96-well plate coated with 200 ng of NRP1 protein and a 96 well-plate coated with 200 ng of BSA as a control group, binding was performed at a concentration of 5 µg/ml per each clone at a room temperature for 1 hour by ELISA (3 times repetition). Thereafter, each well was washed three times with 0.1% TBST, treated with HRP-conjugated HA antibody for 1 hour, washed again, and then incubated with TMB solution for 5 minutes. After the color development reaction was stopped with 2 M sulfuric acid solution, the OD value was measured.

As a result, it was confirmed that 1A03, 3H10 and 4F12 scFv showed specific binding affinity for NRP1, unlike 12B scFv that does not bind to NRP1 (FIG. 6).

Next, in order to measure the binding affinity of each antibody fragment for human NRP1 at varying antibody fragment concentrations, a 96-well plate coated with 200 ng of NRP1 or BSA was treated with each scFv at a concentration of 2,000 ng/ml, 1,000 ng/ml, 500 ng/ml, 250 ng/ml, 125 ng/ml, 62.5 ng/ml, 31.25 ng/ml, or 15.62 ng/ml, and the change in the OD value was analyzed. Regarding the binding affinity for NRP1, the OD value of 12B scFv did not change depending on the concentration change. However, in the case of 1A03, 3H10 and 4F12 scFvs, it could be confirmed through the change in the OD value that the scFv bound to NRP1 increased with compared to BSA as the concentration increased (FIG. 7).

To accurately measure the degree of the binding affinity of the three scFv antibody fragments for NRP1 protein, the final KD value was obtained through ka and kd values by using biacore T100, a surface plasmon resonance (SPR) system. The KD value is the value obtained by dividing the kd value by the ka value. The lower the KD value, the greater the binding affinity for the corresponding substance. The analysis results indicated that 4F12 scFv showed the lowest KD (M) value ($73.60 \times 10^{-9}$), 1A03 scFv showed a KD (M) value of $89.40 \times 10^{-9}$, and 3H10 scFv showed a KD (M) value of $295.4 \times 10^{-9}$ (FIG. 8).

Example 5: Analysis of Binding Affinity of Anti-NRP1 Antibody Fragments Using NRP1-Overexpressing Cell Line After binding affinity for human NRP1 protein was analyzed by ELISA, FACS analysis was performed using patient-derived tumor spheroids with high expression of NRP1 in order to examine whether the antibody fragment would bind to NRP1 present in the actual cell membrane. Each scFv was incubated with $5 \times 10^5$ patient-derived tumor spheroids at 4° C. for approximately 1 hour, and then the cells were washed 3 times with 1 ml of FACS solution. Then, the cells were treated with 1 µg of red fluorescence (PE; phycoerithrin)-labeled HA antibody and incubated at 4° C. for 30 minutes. Next, the cells were washed three times with 1 ml of FACS solution and analyzed using a FACS Caliburm system.

The results of the analysis indicated that the three antibody fragments, including 1A03, 3H10 and 4F12, all did bind specifically to the NRP1-overexpressing cell line compared to the cells treated with PE-conjugated HA antibody and 12B (FIG. 9).

Example 6: Analysis of the Penetration Ability of Anti-NRP1 Antibody Fragments into NRP1-Overexpressing Cancer Cells The intracellular penetration abilities of the three anti-NRP1 antibody fragments were analyzed by cell immunofluorescence staining. A PD-lysine solution was added to a chamber slide and coated at room temperature for 1 to 2 hours. The solution was removed and the slide was dried. Thereafter, the slide was treated with 200 µl of NBA solution containing $5 \times 10^4$ patient-derived tumor spheroids, and then incubated at 37° C. for 4 to 5 hours to fix the cells to the slide. Next, the NBA solution was removed, and the cells were fixed in 4% paraformaldehyde at 4° C. for 10 minutes. After washing three times with PBS, the cells were treated with 0.1% Triton X-100 to increase cell penetration ability. In order to stain the NRP1 protein, the cells were treated with anti-human NRP1 antibody (R&D) and anti-NRP1 antibody fragment at the same time and incubated at 37° C. for 15, 30 and 60 minutes. After washing three times with PBS, the cells were blocked with 1% BSA solution at room temperature for about 1 hour in order to block nonspecific binding. As secondary antibody, green fluorescence (Alexa-Fluor 488)-labeled goat anti-mouse antibody (Invitrogen) was used to visualize the NRP1 protein, and anti-HA antibody (Santacruz biotechnology) was used to visualize the anti-NPR1 antibody fragment, followed by incubation at room temperature for 1 hour. Finally, DAPI staining was performed for nuclear staining. After final washing, the glass cover was fixed onto the slide which was then observed using a confocal laser scanning microscope.

As a result, it could be seen that, in all the three anti-NRP1 antibody fragments, the anti-NRP1 antibody fragment attached to the cell surface and the anti-NRP1 antibody fragments inserted into the cells were mixed at 15 minutes and 30 minutes, but after about 60 minutes, the anti-NRP1 antibody fragments were mostly inserted into the cells by penetration (FIGS. 10a to 10c). In particular, the 4F12 antibody fragment exhibited relatively high cell penetration ability compared to 1A03 and 3H10 with the passage of time (FIG. 10a). These results show that the antibody of the present disclosure can be used for the purpose of delivering a protein expression inhibitory substance or a therapeutic/diagnostic chemical drug into cancer cells.

Example 7: Transformation from Anti-NRP1 Antibody Fragment into NRP1 IgG

In order to transform the anti-NRP1 antibody fragment into an IgG format, the heavy chain and light chain gene sequences of the NRP1 antibody fragment were transfected using an Expi 293F expression system (life technologies). To recover the anti-NRP1 IgG antibody from the culture medium, purification was carried out using an AKTA protein purification system and an Amicon centrifugal filter. The amounts produced were 120 mg/l for IRCR-101 (3H10 converted into IgG format), 66 mg/l for A03, and 15 mg/l for 4F12. In order to confirm the purity of the purified anti-NRP1 IgG antibody, high performance liquid chromatography was used. Since IgG was 150 kD in size, the substance that appeared at 16.388 min at the marker peak was IgG. Three anti-NRP1 IgG antibodies (IRCR-101, 1A03, and 4F12) were detected at this peak, and showed purities of 99.5, 99.4, and 99.5%, respectively (FIG. 13). Limulus Amebocyte Lysate (LAL) QCL-1000™ kit was used to determine endotoxin levels of the three NRP1 antibodies produced. The analysis results indicated that the three antibodies had an endotoxin level of about 0.5-3.1 EU/mg, which corresponds to the normal endotoxin level of a therapeutic protein (FIG. 14).

The binding affinities of the three anti-NRP1 IgG antibodies for human NRP1 were analyzed by ELISA and SPR analysis, and as a result, it was confirmed that the binding affinity was higher in the order of 1A03, IRCR-101 and 4F12. In particular, 4F12 had a KD value of 0.6 nM, which is the binding affinity level of the current therapeutic antibody (FIG. 15). The specific binding affinity for human NRP1 was analyzed by comparison with other proteins having a structure similar to that of human NRP1, and as a result, it was confirmed that all the three anti-NRP1 IgG antibodies did bind only to human NRP1 (FIG. 16).

Example 8: Identification of Binding Epitope of Anti-NRP1 IgG Antibody

Since the binding domain of MNRP1685A is a VEGF domain, MNRP1685A was used as a positive control. Each well of a 96-well plate was coated with hNRP1 protein, and then incubated with 500 nM of IRCR-101 or MNRP1685A at 25° C. for 1 hour, washed with PBST, and then incubated with biotin-conjugated VEGF or Sema3A at room temperature for 15 minutes.

The plate was washed with PBST, and then streptavidin-HRP antibody was added thereto and the TMB color development reaction was analyzed by ELISA. As a result, it could be seen that MNRP1685A and IRCR-101 all did bind to the VEGF165 binding domain (the left panel of FIG. 11).

To identify the binding epitopes of the MNRP1685A and IRCR-101, each well of a 96-well plate was coated with 200 ng of hNRP1 protein, and then incubated with 500 nM of IRCR-101 or MNRP1685A at 25° C. for 1 hours, washed with PBST, and then biotin-conjugated IRCR-101 was treated in MNRP1685A-treated wells and biotin-conjugated MNRP1685A was treated in IRCR-101 treated wells at room temperature for 15 minutes.

The plate was washed with PBST, and then streptavidin-HRP antibody was added thereto and the TMB color development reaction was analyzed by ELISA. As a result, it could be seen that the binding epitopes of the control and IRCR-101 did differ from each other (the right panel of FIG. 11).

Example 9: Analysis of Cancer-Specific Internalization and Binding Affinity Using Cancer Cells and Normal Cells Internalization patterns of the three anti-NRP1 IgG antibodies into cancer cells and normal cells were compared using pHrodo® Red Microscale Labeling Kit (Thermo #p35363). According to the principle of the kit, when an antibody is conjugated with a chromogenic sample and the antibody is outside the cell, it does not develop color. On the other hand, when the antibody enters the cell and the surrounding environment is acidified, it develops color. According to this principle, intracellular internalization of the antibody can be confirmed. Conjugation to the three NRP1 IgG antibodies was performed, and internalization patterns of the conjugated antibodies into patient-derived tumor spheroids and normal HUVEC cells were compared. As a result, internalized antibodies were started to be observed in the patient-derived tumor spheroids from 20 minutes (FIG. 17).

Control IgG, IRCR-101, and 1A03 were injected in a glioblastoma subcutaneous model by an intravenous injection. After 20 hours, they were sacrificed to separate into a single cell through cell dissociation. Then immanence thereof to cancer cells were compared from each other using FACS. In the results of screening only antibodies internalizing into cancer cells through permeabilization, IRCR-101 and 1A03 showed 5 times to 6 times higher mean fluorescence intensity (MFI) than the control IgG. It was also confirmed that the in vivo model had cancer cells-specified immanence as in vitro model as described above (FIG. 18).

At a binding temperature of 4° C., the differences in the binding affinities of IRCR-101 and conventional NRP1 antibody (MNRP antibody, produced in house by synthesizing the sequence disclosed in the patent (WO2011143408)) for normal cells and cancer cells were compared. As a result, it was confirmed that when the antibodies were used at the same concentration, the conventional NRP1 antibody showed a higher binding affinity for the normal cells than for the cancer cells, whereas IRCR-101 showed a specific binding affinity for the cancer cells (FIG. 19).

Example 10: Conformation of Control of Cancer Cell Migration and Downstream Factor Whether the three NRP1 IgG antibodies would inhibit cancer cell migration examined using the glioblastoma cell line U87MG and patient-derived tumor spheroids. After treatment with each antibody, the cells were incubated at 37° C. for 24 hours and then analyzed. As a result, it was confirmed that IRCR-101 and 1A03 each showed more than 50% cancer cell migration inhibition in the two types of cells and 4F12 showed about 40% cancer cell migration inhibition in the patient-derived tumor spheroids (FIG. 20).

The inhibition of migration of the breast cancer cell line MBAMB231 and the lung cancer cell line A549 by the final anti-NRP1 IgG antibody IRCR-101 was observed, and as a result, it was confirmed that the antibody inhibited cancer cell migration in a concentration-dependent manner. It was confirmed that when the cells were treated with IRCR-101 (10 μg/ml), the antibody showed 60% cancer cell migration inhibition in the breast cancer model and 30% cancer cell migration inhibition in the lung cancer model (FIG. 21).

In order to examine a change in related signaling substances upon treatment with IRCR-101, changes in NRP1, AKT and ERK in glioblastoma patient-derived tumor spheroids at 15, and 120 min were analyzed by immunoblotting. It was confirmed that NRP1 disappeared at 30 minutes due to complete degradation and that AKT and ERK inhibited the related signaling mechanisms since the phosphorylated AKT and ERK decreased (FIG. 22).

Example 11: Evaluation of Efficacy of IRCR-101 in in Vivo Models and Observation of Target Two subcutaneous models were constructed using glioblastoma patient-derived tumor spheroids and injected intravenously with 5 mg/kg of IRCR-101, three times a week, and the size of the volume was measured. The antibody showed 30-40% tumor size reduction, and the TUNEL assay using immunofluorescence indicated that apoptosis was increased by IRCR-101 (FIG. 23).

Subcutaneous models were constructed using the glioblastoma cell line U87MG and used to compare the efficacy of IRCR-101 with that of the conventional antibody MNRP1685A (MNRP1685A antibody, constructed in-house by synthesizing the sequence disclosed in the patent (WO2011143408 A1)). In the groups administered with 5 mg/kg of each antibody twice a week, MNRP1685A showed 60% tumor growth inhibition, and IRCR-101 showed 80% tumor growth inhibition (FIG. 24).

Subcutaneous models were constructed using the lung cancer cell line A549 and used to compare the efficacy of IRCR-101 with that of the conventional antibody MNRP1685A. In the groups administered with 25 mg/kg of each antibody twice a week, MNRP1685A showed 19% tumor growth inhibition, and IRCR-101 showed 57% tumor growth inhibition (FIG. 25).

In glioblastoma orthotopic models, IRCR-101 was labeled with a fluorescent substance and injected intravenously into the models, and the time-dependent change in the fluorescence intensity was observed at 15 min, 1 hr, 1 day and 2 day. As a result, it was confirmed that on day 1, strong fluorescence appeared at the site corresponding to the tumor site, and up to day 3, fluorescence appeared at the same site (FIG. 26).

Example 12: Evaluation of Distribution in Normal Tissues Using Monkey TMA

In order to examine the side effects of IRCR-101 and the conventional NRP1 antibody (MNRP1685A antibody, constructed in-house by synthesizing the sequence disclosed in the patent (WO2011143408 A1)), TMA (Tissue microArray) was performed using male and female monkeys. The results of the analysis indicated that IRCR-101 had little or no binding affinity for most normal organ tissues, unlike the conventional NRP1 antibody. The fact that IRCR-101 has little or no binding affinity for normal tissues suggests that IRCR-101 will show less side effects in clinical trials (FIG. 27).

INDUSTRIAL APPLICABILITY

The screening method according to the present disclosure uses patient-derived tumor spheroids, and thus can screen an antibody that targets a protein overexpressed specifically in a patient. The antibody screened according to the present disclosure may be used to produce a patient-specific antibody, and thus is useful for the development of a patient-specific therapeutic drug. In addition, the antibody or antigen-binding fragment thereof screened by the method of the present disclosure is expected to have a high possibility of success in future clinical trials. Furthermore, the screening method according to the present disclosure can screen an internalizing antibody, and thus makes it possible to screen an antibody suitable for production of a drug-antibody conjugate (ADC).

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A method for screening an antibody or an antigen-binding fragment thereof, which binds to NRP1 and is internalized in to cells of tumor spheroids, the method comprising the steps of:
   (i) treating patient-derived tumor spheroids, which express NRP1, with a library comprising antibodies or antigen-binding fragments thereof, and then firstly screening antibodies or antigen-binding fragments thereof which bind to NRP1 and are internalized in to cells of the tumor spheroids by performing phage display;
   (ii) treating patient-derived tumor spheroids, which do not express the NRP1, with the first screened antibodies or antigen-binding fragments thereof to perform negative selection on antibodies or antigen-binding fragments thereof binding to the patient-derived tumor spheroids which do not express the NRP1;
   (iii) administering the antibodies or antigen-binding fragments thereof, obtained by separating/removing antibodies or antigen-binding fragments thereof that binds to the patient-derived tumor spheroids of step (ii) from the antibodies or antigen-binding fragments thereof screened in step (i), to animal models transplanted with patient-derived tumor spheroids which overexpress the NRP1 by intratumoral injection, and dissociating cancer tissues of the animal models into single cells to secondly screen antibodies or antigen-binding fragments which bind to NRP1; and
   (iv) separating or removing antibodies or antigen-binding fragments thereof, which bind to an antigen other than the NRP1, from the second screened antibodies or antigen-binding fragments thereof.

2. The method of claim 1, wherein the antibody or antigen-binding fragment thereof is internalized into cells.

3. The method of claim 1, wherein the patient-derived tumor spheroids which overexpress the NRP1 are obtained by performing the following steps:
   (a) dissociating isolated cancer patient-derived cancer tissue, and collecting a cell fraction from the dissociated tissue; and
   (b) treating the collected cell fraction with protease, followed by filtration, centrifugation and suspension, thereby obtaining single cells.

4. The method of claim 1, wherein the animal models transplanted with the patient-derived tumor spheroids overexpressing the NRP1 are immunodeficient mice.

5. The method of claim 4, wherein the immunodeficient mice are nude mice, NOD (non-obese diabetic) mice, SCID (Severe combined immunodeficiency) mice, NOD-SCID mice, or NOG (NOD/SCID Il2rg−/−) mice.

6. The method of claim 1, further comprising a step of converting the antibody or antigen-binding fragment thereof screened by the method to an IgG format.

* * * * *

UNITED STATES PATENT AND TRADEMARK OFFICE
CERTIFICATE OF CORRECTION

PATENT NO. : 11,085,930 B2  
APPLICATION NO. : 16/306568  
DATED : August 10, 2021  
INVENTOR(S) : Do-Hyun Nam Page 1 of 1

It is certified that error appears in the above-identified patent and that said Letters Patent is hereby corrected as shown below:

In the Specification

Column 7, Line 65, "(A)" should be -- ($\lambda$) --.

Column 20, Line 48, "pill" should be -- pIII --.

Column 21, Line 61, "Caliburm" should be -- Calibur™ --.

Column 22, Line 54, "AKTA" should be -- ÄKTA --.

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*